(12) United States Patent
Taylor et al.

(10) Patent No.: US 10,258,606 B2
(45) Date of Patent: *Apr. 16, 2019

(54) ENDOTHELIN SINGLE NUCLEOTIDE POLYMORPHISMS AND METHODS OF PREDICTING β-ADRENERGIC RECEPTOR TARGETING AGENT EFFICACY

(71) Applicant: The Regents of the University of Colorado, A Body Corporate, Denver, CO (US)

(72) Inventors: Matthew R. G. Taylor, Denver, CO (US); Luisa Mestroni, Boulder, CO (US)

(73) Assignee: The Regents of the University of Colorado, A Body Corporate, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/746,362

(22) Filed: Jun. 22, 2015

(65) Prior Publication Data

US 2015/0366843 A1    Dec. 24, 2015

Related U.S. Application Data

(63) Continuation of application No. 12/670,966, filed as application No. PCT/US2008/071342 on Jul. 28, 2008, now Pat. No. 9,062,347.

(Continued)

(51) Int. Cl.
    *C12Q 1/68*    (2018.01)
    *A61K 31/4045*    (2006.01)
    (Continued)

(52) U.S. Cl.
    CPC ........ *A61K 31/4045* (2013.01); *A61K 31/404* (2013.01); *C12Q 1/6883* (2013.01);
    (Continued)

(58) Field of Classification Search
    None
    See application file for complete search history.

(56) References Cited

U.S. PATENT DOCUMENTS

| 6,066,502 A | 5/2000 | Kroger et al. | 435/455 |
| 6,821,991 B2 | 11/2004 | Hu | 514/329 |
| 7,678,824 B2 | 3/2010 | Liggett et al. | 514/415 |

FOREIGN PATENT DOCUMENTS

| WO | WO 2005/025409 | 3/2005 |
| WO | WO 2006/031955 | 3/2006 |

(Continued)

OTHER PUBLICATIONS

Juppner; Bone, vol. 17; 1995, pp. 39S-40S.*

(Continued)

*Primary Examiner* — Jehanne S Sitton
(74) *Attorney, Agent, or Firm* — Norton Rose Fulbright US LLP

(57) ABSTRACT

The present invention concerns the use of methods for evaluating β-adrenergic receptor targeting agent treatment for a patient, particularly one with a heart condition. In general, the disclosed methods entail determining the presence or absence of one or more polymorphisms in an endothelin gene system member. Based on the results of this determination, a β-adrenergic receptor targeting agent may be prescribed, administered or a treatment regimen altered, including the administration of a β-blocker. Accordingly, methods of treatment are also described.

6 Claims, 4 Drawing Sheets

Specification includes a Sequence Listing.

Related U.S. Application Data

(60) Provisional application No. 60/952,441, filed on Jul. 27, 2007.

(51) Int. Cl.
 *A61K 31/404* (2006.01)
 *C12Q 1/6883* (2018.01)
(52) U.S. Cl.
 CPC . *C12Q 2600/106* (2013.01); *C12Q 2600/156* (2013.01); *C12Q 2600/172* (2013.01); *Y10T 436/143333* (2015.01)

(56) References Cited

FOREIGN PATENT DOCUMENTS

| WO | WO 2006/137487 | * 12/2006 | .................... 435/6.1 |
|---|---|---|---|
| WO | WO 2007/041680 | 4/2007 | |

OTHER PUBLICATIONS

Lucentini (The Scientist; 2004, vol. 24, p. 20).*
Hegele (Arterioscler. Thromb. Vasc. Biol.; 2002, vol. 22, pp. 1058-1061).*
Liggett et al; PNAS, vol. 103, Jul. 25, 2006, pp. 11288-11293.*
Arinami et al., "Chromosomal assignments of the human endothelin family genes: the endothelin-1 gene (EDN1) to 6p23-p24, the endothelin-2 gene (EDN2) to 1p34, and the endothelin-3 gene (EDN3) to 20q13.2-q13.3," Am. J. Hum. Genet., 48:990-996, 1991.
Barden et al., "Association between the endothelin-1 gene Lys198Asn polymorphism blood pressure and plasma endothelin-1 levels in normal and pre-eclamptic pregnancy," J. Hypertens., 19:1775-82, 2001.
*Beta-Blocker Evaluation of Survival Trial Investigators*. "A trial of the beta-blocker bucindolol in patients with advanced chronic heart failure," N. Engl. J. Med., 344:1659-67, 2001.
Bianchetti et al., "In vitro inhibition of intestinal motility by phenylethanolaminotetralines: evidence of atypical beta-adrenoceptors in rat colon," Br. J. Pharmacol., 100:831-839, 1990.
Bond et al., "Agonist and antagonist characterization of a putative adrenoceptor with distinct pharmacological properties from the alpha- and beta-subtypes," Br. J. Pharmacol., 95:723-734, 1988.
Bristow et al., "Beta 1- and beta 2-adrenergic-receptor subpopulations in nonfailing and failing human ventricular myocardium: coupling of both receptor subtypes to muscle contraction and selective beta 1-receptor down-regulation in heart failure," Circ. Res., 59(3):297-309, 1986.
Bristow et al., "Beta 1- and beta 2-adrenergic receptor-mediated adenylate cyclase stimulation in nonfailing and failing human ventricular myocardium," Mol. Pharmacol., 35:296-303, 1989.
Brodde et al., "Regional distribution of beta-adrenoceptors in the human heart: coexistence of functional beta 1- and beta 2-adrenoceptors in both atria and ventricles in severe congestive cardiomyopathy," J. Cardiovasc. Pharmacol., 8:1235-1242, 1986.
Brodde et al., "Importance of beta 2-adrenergic receptors in heart failure," Z. Kardiol., 81:71-78, 1992. (English Abstract).
Brugada et al., "Role of candidate modifier genes on the phenotypic expression of hypertrophy in patients with hypertrophic cardiomyopathy," J. Investig. Med., 45:542-51, 1997.
Charron et al., "Identification of a genetic risk factor for idiopathic dilated cardiomyopathy. Involvement of a polymorphism in the endothelin receptor type A gene ," Eur. Heart J., 20:1587-91, 1999.
CIBIS-II Investigators, "The Cardiac Insufficiency Bisoprolol Study II (CIBIS-II): a randomised trial," Lancet, 353:9-13, 1999.
Coleman et al., "Beta-adrencoceptors in guinea-pig gastric fundus—Are they the same the as the 'atypical' beta-adrenoreceptors in rat adipocytes?" Brit. J. Pharmacology Proc. Supl., 90:40, 1987.
Diefenbach et al., "Systematic analysis of sequence variability of the endothelin-1 gene: A prerequisite for association studies," Genetic Testing, 10(3):163-168, 2006.
Dohlman et al., "Model systems for the study of seven-transmembrane-segment receptors,"Annu. Rev. Biochem., 60:653-688, 1991.
DZAU, "The role of mechanical and humoral factors in growth regulation of vascular smooth muscle and cardiac myocytes," Curr. Opin. Nephrol. Hypertens., 2:27-32, 1993.
Emorine et al., "Molecular characterization of the human beta 3-adrenergic receptor," Science, 245:1118-1121, 1989.
Emoto and Yanagisawa, "Endothelin-converting enzyme-2 is a membrane-bound, phosphoramidon-sensitive metalloprotease with acidic pH optimum," J. Biol. Chem., 270:15262-15268, 1995.
Evans et al., "Moving towards individualized medicine with pharmacogenomics," Nature, 429:464-8, 2004.
Frantz et al., "Baseline and serial neurohormones in patients with congestive heart failure treated with and without bucindolol: results of the neurohumoral substudy of the Beta-blocker Evaluation of Survival Study (BEST)" Journal of Cardiac Failure, 13(2):437-444, 2007.
Frielle et al., "Cloning of the cDNA for the human beta 1-adrenergic receptor," Proc. Natl. Acad. Sci. USA, 84:7920-7924, 1987.
Garnier et al., "GOR method for predicting protein secondary structure from amino acid sequence," Methods Enzym., 266:540-53, 1996.
Giannessi et al., "The role of endothelins and their receptors in heart failure," Pharmacol. Res., 43:111-26, 2001.
Granneman et al., "CGP 12177A modulates brown fat adenylate cyclase activity by interacting with two distinct receptor sites," J. Pharmacol. Exp. Ther., 256:421-425, 1991.
Hallberg et al., "Gender-specific association between preproendothelin-1 genotype and reduction of systolic blood pressure during antihypertensive treatment—results from Swedish Irbesartan Left Ventricular Hypertrophy Investigation versus Atenolol (SILVHIA)," Clinical Cardiology, 27(5):287-290, 2004.
Herrmann et al., "A polymorphism in the endothelin-A receptor gene predicts survival in patients with idiopathic dilated cardiomyopathy," Eur. Heart. J., 22:1948-53, 2001.
Hiroe et al., "Plasma endothelin-1 levels in idiopathic dilated cardiomyopathy," Am. J. Cardiol., 68:1114-5, 1991.
Hjalmarson et al., "Effects of controlled-release metoprolol on total mortality, hospitalizations, and well-being in patients with heart failure: the Metoprolol CR/XL Randomized Intervention Trial in congestive heart failure (MERIT-HF). MERIT-HF Study Group," J. Am. Med. Assoc., 283:1295-1302, 2000.
Iemitsu et al., "Polymorphism in endothelin-related genes limits exercise-induced decreases in arterial stiffness in older subjects," Hypertension, 47:928-936, 2006.
Iglarz et al., "Preproendothelin-1 gene polymorphism is related to a change in vascular reactivity in the human mammary artery in vitro," Hypertension, 39:209-13, 2002.
Ikeda et al., "Molecular isolation and characterization of novel four subisoforms of ECE-2," Biochem. Biophys. Res. Commun., 293:421-426, 2002.
Inoue et al., "The human endothelin family: three structurally and pharmacologically distinct isopeptides predicted by three separate genes," Proc. Natl. Acad. Sci. USA, 86:2863-2867, 1989.
International Preliminary Report on Patentability, issued in International Application No. PCT/US2008/071342, dated Feb. 2, 2010.
Jin et al., "Association of endothelin-1 gene variant with hypertension," Hypertension, 41:163-7, 2003.
Jones, "Protein secondary structure prediction based on position-specific scoring matrices," J. Mol. Biol., 292:195-202, 1999.
Kaandorp et al., "Prediction of beneficial effect of beta blocker treatment in severe ischaemic cardiomyopathy: assessment of global left ventricular ejection fraction using dobutamine stress cardiovascular magnetic resonance," Heart, 91:1471-1472, 2005.
King et al., "Evaluation of regulatory potential and conservation scores for detecting cis-regulatory modules in aligned mammalian genome sequences," Genome Res., 15:1051-60, 2005.
Ko et al., "Endothelin-2 in ovarian follicle rupture," Endocrin., 147:1770-1779, 2006.

(56) References Cited

OTHER PUBLICATIONS

Kobilka et al., "cDNA for the human beta 2-adrenergic receptor: a protein with multiple membrane-spanning domains and encoded by a gene whose chromosomal location is shared with that of the receptor for platelet-derived growth factor," Proc. Natl. Acad. Sci. USA, 84:46-50, 1987.

Kolbe et al., "Regulatory potential scores from genome-wide three-way alignments of human, mouse, and rat," Genome Res., 14:700-7, 2004.

Kozak et al., "Endothelin-1 gene polymorphism in patients with malignant arrhythmias," J. Cardiovasc. Pharmacol., 44:S92-S95, 2004.

Krum et al., "Changes in plasma endothelin-1 levels reflect clinical response to beta-blockade in chronic heart failure," Am. Heart J., 131:337-41, 1996.

Leizorovicz et al., "Bisoprolol for the treatment of chronic heart failure: a meta-analysis on individual data of two placebo-controlled studies—CIBIS and CIBIS II. Cardiac Insufficiency Bisoprolol Study," Am. Heart J., 143(2):301-307, 2002.

Levin, "Endothelins," N. Engl. J. Med., 333:356-63, 1995.

Liggett et al., "Pharmacology and molecular biology of adrenergic receptors," In: Catecholamines, Bouloux (Ed.), W. B. Sounders, London, p. 279-306, 1993.

Liggett et al., "A polymorphism within a conserved β1-adrenergic receptor motif alters cardiac function and β-blocker response in human heart failure ," Proc. Natl. Acad. Sci. USA, 103:11288-93, 2006.

Lowes et al., "Differential effects of beta-1 polymorphisms on mortality, hospitalizations, and myocardial infarctions with bucindolol therapy," Journal of Cardiac Failure, 12(6):S87, 2006.

Mcmurray et al., "Plasma endothelin in chronic heart failure," Circulation, 85:1374-9, 1992.

Meiden et al., "Endothelin-converting enzyme-1, abundance of isoforms a-d and identification of a novel alternatively spliced variant lacking a transmembrane domain," J. Biol. Chem., 280:40867-40874, 2005.

Miyauchi et al., "Pathophysiology of endothelin in the cardiovascular system," Annu. Rev. Physiol., 61:391-415, 1999.

Nahmias et al., "Molecular characterization of the mouse beta 3-adrenergic receptor: relationship with the atypical receptor of adipocytes," J. EMBO, 16(12):3721-3727, 1991.

Nambi et al., "Endothelin and heart failure," Heart Fail. Rev., 6:335-40, 2001.

Nicaud et al., "Polymorphisms of the endothelin-A and -B receptor genes in relation to blood pressure and myocardial infarction," Am. J. Hypertens., 12:304-10, 1999.

Packer et al., "Effect of carvedilol on the morbidity of patients with severe chronic heart failure: results of the carvedilol prospective randomized cumulative survival (COPERNICUS) study," Circulation, 106(17):2194-2199, 2002.

Pertea et al., "GeneSplicer: a new computational method for splice site prediction," Nucleic Acids Res., 29:1185-90, 2001.

Rossi et al., "Genetic variation in the endothelin system: do polymorphisms affect the therapeutic strategies?" Annals of the New York Academy of Sciences, 1069:34-50, 2006.

Small et al., "Synergistic polymorphisms of beta1- and alpha2C-adrenergic receptors and the risk of congestive heart failure," N. Engl. J. Med., 347:1135-1142, 2002.

Spieker and Luscher, "Will endothelin receptor antagonists have a role in heart failure," Med. Clin. North Am., 87:459-74, 2003.

Spieker et al., "Endothelin receptor antagonists in congestive heart failure: a new therapeutic principle for the future?" J. Am. Coll. Cardiol., 37:1493-505, 2001.

Stevens and Brown, "Genetic Variability of the ET-1 and the ETA Receptor Genes in Essential Hypertension," J. Cardiovasc. Pharmacol., 26 Suppl 3:S9-12, 1995.

Tanaka et al., "Evaluation of the Lys198Asn and -134delA genetic polymorphisms of the endothelin-1 gene," Hypertens. Res., 27:367-71, 2004.

Taylor et al., "Pharmacogenetic effect of an endothelin-1 haplotype on response to bucindolol therapy in chronic heart failure," Pharmacogenetics and Genomics, 19(1): 35-43, 2009.

Tiret et al., "The Lys198Asn Polymorphism in the Endothelin-1 Gene Is Associated With Blood Pressure in Overweight People," Hypertension, 33:1169-74, 1999.

Turner et al., "The neprilysin (NEP) family of zinc metalloendopeptidases: genomics and function," Bioessays, 23:261-269, 2001.

Valdenaire et al., "A fourth isoform of endothelin-converting enzyme (ECE-1) is generated from an additional promoter: Molecular cloning and characterization ," Eur. J. Biochem., 264:341-349, 1999.

Vasku et al., "The double heterozygote of two endothelin-1 gene polymorphisms (G8002A and -3A/-4A) is related to big endothelin levels in chronic heart failure," Exp. Mol. Pathol., 73:230-3, 2002.

Wei et al., "Endothelin in human congestive heart failure," Circulation, 89:1580-6, 1994.

Weinshilboum, "Inheritance and drug response," N. Engl. J. Med., 348:529-37, 2003.

Wilkinson, "Drug metabolism and variability among patients in drug response," N. Engl. J. Med., 352:2211-21, 2005.

Yanagisawa et al., "A novel potent vasoconstrictor peptide produced by vascular endothelial cells," Nature, 332:411-5, 1988.

Yang-Feng et al., "Chromosomal organization of adrenergic receptor genes," Proc. Natl. Acad. Sci. USA, 87:1516-1520, 1990.

Zhang et al., "Expression of endothelins and their receptors in nonmelanoma skin cancers," J. Cutan. Med. Surg., 10:269-276, 2006.

\* cited by examiner

FIG. 4

ENDOTHELIN SINGLE NUCLEOTIDE POLYMORPHISMS AND METHODS OF PREDICTING β-ADRENERGIC RECEPTOR TARGETING AGENT EFFICACY

This application is a continuation of U.S. patent application Ser. No. 12/670,966, filed Jan. 27, 2010, now U.S. Pat. No. 9,062,347, which is a national phase application under 35 U.S.C. § 371 of International Patent Application No. PCT/US2008/071342 filed Jul. 28, 2008 which claims priority to U.S. Provisional Application No. 60/952,441 filed Jul. 27, 2007, each of which is incorporated herein by reference in its entirety.

This invention was made with government support under grant numbers NIH-1K23H167915-01A1, HL69071-01 and GM062628-05 awarded by the National Institutes of Health. The government has certain rights in the invention.

BACKGROUND OF THE INVENTION

1. Field of the Invention

The present invention relates to pharmacogenetics and cardiology. More specifically, the present invention relates, in part, to methods of predicting the efficacy of β-adrenergic receptor targeting agent treatment in a patient with a cardiovascular condition based on the patient's genotype of certain polymorphisms in endothelin gene system members.

2. Description of Related Art

According to the American Heart Association (AHA), about 79 million Americans have some form of cardiovascular disease, which can include high blood pressure, coronary heart disease (heart attack and chest pain), cardiomyopathy, stroke, birth defects of the heart and blood vessels, and congestive heart failure, and close to a million die from such conditions every year. The annual report of the AHA further states that cardiovascular disease kills more Americans than the next seven causes of death combined, including cancer. Heart disease accounted for 40% of all deaths in the U.S. in 1999, and mortality from heart failure is approximately 50% within 5 years.

In the United States alone there are approximately six million people, about 1.5% of the population, with chronic heart failure ("HF"), and roughly 550,000 new patients are diagnosed each year. Medical therapy has made progress in treating HF, but morbidity and mortality remain high (Mann et al., 2005). The current standard of care in HF involves the use of inhibitors (ACE inhibitors, ARBs, and/or aldosterone receptor antagonists) of the renin-angiotensin-aldosterone system (RAAS), and β-blockers, which competitively inhibit β-adrenergic receptors on cardiac myocytes. β-blocker therapy is standard treatment for systolic heart failure and reduces allcause mortality by 34-65% (CIBIS-II Investigators, 1999; Packer et al., 1996; Packer et al., 2001). These data are in agreement with other large drug trials where only between 25-60% of patients benefit from exposure to medication as compared to placebo (Wilkinson, 2005; Evans and Relling, 2004; Weinshilboum, 2003).

Even though most β-blocker trials in heart failure have shown group beneficial effects, there is substantial interindividual variability in outcome that is not explained by baseline clinical characteristics (CIBIS-II Investigators, 1999). Interindividual variability in the response to pharmacologic therapy is recognized with virtually all drugs. In circumstances such as the treatment of chronic heart failure with β-blockers—where morbidity and mortality are high, the titration algorithm is complex, the interindividual variability is substantial, and additional treatment options exist—assessing the likelihood of a favorable (or adverse) long-term response to drug therapy can have a significant impact on decision making.

Another cardiovascular disease, cardiomyopathy, is a disease of the heart muscle. This form of cardiovascular disease is often distinctive, both in general symptoms and in patterns of blood flow, thus facilitating diagnosis. Increasing recognition of this disease, along with improved diagnostic techniques, have shown that cardiomyopathy is a major cause of morbidity and mortality. In some areas of the world it may account for as many as 30% of all deaths due to heart disease.

Several types of cardiomyopathy are known, including ischemic, dilated, hypertrophic, restrictive and idiopathic (and combinations thereof). The prognosis for all types of these diseases is often poor. For example, the survival rate of dilated cardiomyopathy for five years is typically 50 to 60%. Treatment of cardiomyopathy involves restricted activity, stress avoidance, treatment with β-blockers, prophylactic antibiotic therapy, use of anti-coagulants, calcium channel blockers, surgery and cardiac transplantation. With this variety of treatments available, it would be helpful to identify which patients would benefit the most from one treatment as compared to another. For example, dobutamine stress cardiovascular magnetic resonance has been employed to predict whether or not β-blocker treatment of patients exhibiting severe ischemic cardiomyopathy will be beneficial (Kaandorp 2005). However, the small number of patients tested limits the significance and clinical applicability of these findings. Other means of predicting which patients will benefit from β-blocker treatment are also needed.

SUMMARY OF THE INVENTION

The present invention provides methods for individualized therapy based on the identification of polymorphisms in endothelin gene system members that affect an individual's response to β-adrenergic receptor targeting agents, such as β-blockers. In certain embodiments, the present invention concerns individualized therapy for heart failure.

The invention is based, in part, on the determination by the inventors that certain single nucleotide polymorphisms (SNPs) in an endothelin (EDN) gene system member of a patient suffering from a medical condition render that patient amenable to treatment with a β-adrenergic receptor targeting agent. For example, as discussed in more detail below, alleles represented by two EDN1 SNPs, Lys198Asn and G/A (Intervening sequence (IVS)-4)), commonly appearing in one of two complementary haplotypes, showed a strong pharmacogenetic interaction with bucindolol therapy on time to first heart failure hospitalization or all cause mortality. These results appear to represent the first study to identify a haplotype associated with clinical response to a β-blocker in dilated cardiomyopathy. The findings discussed herein demonstrate that certain EDN-related genetic predictors of outcome may identify a large subpopulation of patients who may benefit from β-adrenergic receptor targeting agent treatment.

Accordingly, in one general aspect, the present invention contemplates a method for evaluating β-adrenergic receptor targeting agent treatment of a patient comprising determining the presence or absence of at least one polymorphism in an endothelin gene system member of the patient, wherein the information is predictive of β-adrenergic receptor targeting agent efficacy in the patient. Methods of the present invention also include assessing whether to prescribe or administer a β-adrenergic receptor targeting agent to a patient with a medical condition, such as cardiovascular disease, comprising obtaining information from the patient regarding his/her polymorphisms in endothelin gene system members and/or their encoded gene products that affect a response to a β-adrenergic receptor targeting agent. In certain embodiments, knowledge about which polymorphism a patient has at (i) nucleotide position +356 in intron 4 of EDN1 (rs2071942) or (ii) nucleotide position +61 in exon 5 of EDN1 (rs5370) encoding a polymorphism at amino acid 198 of EDN1 protein provides the basis for assessing whether to administer or prescribe a β-adrenergic receptor targeting agent to the patient. The terms "rs2071942" and "rs5370" refer to the Reference SNP (rs) identification numbers used in standard nomenclature by the National Center for Biotechnology Information (NCBI).

It is generally understood that polymorphisms occur in the context of genes; however, in the case of polymorphisms that affect the encoded gene product, an alteration in that gene product may also be referred to as a polymorphism. For example, in certain embodiments, at least one polymorphism is at (i) nucleotide position +356 in intron 4 (that is, with initial base of intron 4 as position +1) of EDN1 (rs2071942) or (ii) nucleotide position +61 in exon 5 (that is, with initial base of exon 5 as position +1) of EDN1 (rs5370) encoding a polymorphism at amino acid 198 of EDN1 protein, wherein the patient is being considered for treatment with a β-adrenergic receptor targeting agent.

An "endothelin gene system member" of the present invention may be any gene that encodes an endothelin protein or encodes a protein that directly operates on, or interacts with, or alters expression or regulation of, an endothelin. Non-limiting examples of endothelin gene system members include any endothelin gene, any endothelin receptor (EDNR) gene, or any endothelin converting enzyme (ECE) gene. In particular embodiments, the endothelin gene system member is an endothelin gene. In certain embodiments, the endothelin gene is EDN1, EDN2, or EDN3. In particular embodiments, the endothelin gene is EDN1. In certain embodiments, the endothelin gene system member is an endothelin receptor gene, such as EDNRA or EDNRB. In certain embodiments, the endothelin gene system member is an endothelin converting enzyme gene, such as ECE1 or ECE2. Proteins encoded by endothelin gene system members are also encompassed by the present invention.

As used herein, a "β-adrenergic receptor targeting agent" refers to a substance and/or pharmacological agent that interacts with one or more members of the β-adrenergic receptor protein system. In certain embodiments, the β-adrenergic receptor targeting agent is a β-blocker. The β-blocker may be a non-selective β-blocker, as described below. In certan embodiments, the non-selective β-blocker is selected from the group consisting of bucindolol, carteolol, carvedilol, carvedilol phosphate, nadolol, prebutolol sulfate, pindolol, propanolol hydrochloride, sotalol hydrochloride, or rimolol maleate or a selective β-blocker, as described below. The β-blocker may be a selective β-blocker, as described below. In certain embodiments, the selective β-blocker is selected from the group consisting of acebutolol, atenolol, betaxolol hydrochloride, bisoprolol, esmolol, metaprolol succinate, or metoprolol tartrate. In particular embodiments, the β-adrenergic receptor targeting agent is bucindolol. In particular embodiments, the β-adrenergic receptor targeting agent is specifically not bucindolol.

The present invention is also concerned with obtaining information regarding a polymorphism in an endothelin gene system member directly or as deduced by determining the nucleotide sequence at a certain position, and prescribing or administering a β-adrenergic receptor targeting agent based on the obtained information. Such certain positions may include, for example, (i) nucleotide position +356 in intron 4 of EDN1 (rs2071942) and/or (ii) nucleotide position +61 in exon 5 of EDN1 (rs5370) encoding a polymorphism at amino acid 198 of EDN1 protein. It will be understood that cognate nucleic acids for proteins encoded by endothelin gene system members include the mRNA transcript encoding the protein, both strands of any cDNA generated from the mRNA transcript, and both strands of the genomic DNA for the endothelin gene system member genes.

The invention provides a method for determining whether a β-adrenergic receptor targeting agent should be prescribed to a patient wherein the identity of a polymorphic nucleotide or amino acid site of an endothelin gene system member is determined and based on the results of that determination, a β-adrenergic receptor targeting agent is either prescribed or not. Similarly, based on the genotype, another medication may be prescribed for patient with the unfavorable genotype, so as to attempt to gain improved clinical response. In both scenarios, drug treatment decisions are based on the endothelin gene system member genotype of the patient.

Any method of the present invention may be employed with respect to a patient who has symptoms of or is suffering from a medical condition. As used herein, "medical condition" includes but is not limited to any condition or disease manifested as one or more physical and/or psychological symptoms for which treatment is desirable, and includes previously and newly identified diseases and other disorders having similar pathophysiological states. For example, a medical condition may be a cardiovascular disease. As used herein, a "cardiovascular disease" is any abnormal condition characterized by the dysfunction of the heart or blood vessels. Some examples of cardiovascular diseases are disclosed, e.g., in Yale University School of Medicine Heart Book, Chapter 23, Cardiovascular Drugs, Apr. 16, 1999; Mosby's Medical, Nursing, & Allied Health Dictionary, 1998; and Stedman's Medical Dictionary, 1990. Non-limiting examples of medical conditions include, heart failure (HF), cardiac arrhythmias, hypertension, dilated cardiomyopathy and ischemic heart disease (cardiomyopathy, angina, myocardial infarction). In certain embodiments, the patient has symptoms of or has been diagnosed with a medical condition comprising heart failure or cardiomyopathy. In certain embodiments, the patient has symptoms of or has been diagnosed with heart failure. In certain embodiments, the patient has symptoms of or has been diagnosed with dilated cardiomyopathy. The present invention further identifies patients that will positively respond to treatment using a β-adrenergic receptor targeting agent.

In some embodiments, methods include identifying a patient possibly in need of treatment with a β-adrenergic receptor targeting agent, such as a β-blocker. A patient for which a β-adrenergic receptor targeting agent is being considered as a treatment option may have symptoms of or may have been diagnosed with a medical condition, as described herein. In certain embodiments, the patient has symptoms of or has been diagnosed with cardiomyopathy, such as dilated cardiomyopathy. In particular embodiments, a patient has symptoms of or has been diagnosed with heart failure. The heart failure may be considered advanced heart failure, though the invention may not be limited to such patients. The term "advanced heart failure" is used according to its ordinary and plain meaning in the field of cardiology. In some embodiments, a patient being prescribed a β-adrenergic receptor targeting agent may have class III or class IV heart failure according to the NYHA classification system. The NYHA classification system is one evaluation system; however, it is contemplated that the invention is not limited in this way and that this is meant to be illustrative rather than limiting. Patients may be classified by another such system. It is futher contemplated that patients may be classified by a different methodology but that the invention would be implemented similarly.

In other embodiments, however, a patient may have signs or symptoms of heart failure but not advanced heart failure. In such a situation the patient may have been or may be characterized as a class I or II heart failure patient according to the NYHA classification system. In these embodiments, the patient may be genotyped for a polymorphism as described herein, in which case a person is a candidate for β-adrenergic receptor targeting agent treatment. Consequently, methods of the invention can involve preventing heart failure in a patient by determining whether the patient has a polymorphism as described herein and administering a β-adrenergic receptor targeting agent if s/he does. Certain patients might be particularly suited for this including, but not limited to, those patients with symptoms of heart failure, with risk factors of heart failure, or with a familial or prior history of heart failure.

A further method of the present invention contemplates a method for evaluating whether a heart failure patient will respond positively to a β-adrenergic receptor targeting agent comprising determining (i) the presence or absence of a polymorphism at nucleotide position +356 in intron 4 of EDN1 (rs2071942) of the patient, and/or (ii) the presence or absence of a polymorphism at nucleotide position +61 in exon 5 of EDN1 (rs5370).

In methods of the present invention, determining the presence or absence of at least one polymorphism may be performed via any method known to those of skill in the art. Those of skill in the art readily understand that the coding sequence of a gene refers to the strand of the gene that is used for transcription of messenger RNA. The sequence of the coding sequence is complementary to the sequence of the transcribed transcript. Because of the complementary nature of sequences between a coding sequence and a noncoding sequence, the sequence of any coding sequence can be determined by knowing the sequence of the transcript, the noncoding strand, or the encoded protein. The nucleic acid sequence at that position in one or both alleles can be determined by a number of ways known to those of skill in the art. In certain embodiments, determining the presence or absence of at least one polymorphism comprises pyrosequencing, chain terminating sequencing, restriction digestion, allele-specific polymerase reaction, single-stranded conformational polymorphism analysis, genetic bit analysis, temperature gradient gel electrophoresis, ligase chain reaction, or microarray hybridization.

Alternatively, the sequence of a protein encoded by an endothelin gene system member may be evaluated. This evaulation may take place via any method known to those of skill in the art. Methods for determining the sequence at a particular position in a protein are well known and may involve using, for example, an antibody, high pressure liquid chromatography, or mass spectroscopy. In certain embodiments, the amino acid at position 198 in one or more of the patient's EDN1 proteins is known. It is contemplated that any sample evaluated from the patient will contain multiple endothelin gene system member proteins that can be analyzed.

In any method of the present invention, a patient's genotype at nucleotide position +356 in intron 4 of EDN1 (rs2071942) may be known. Alternatively, in any method of the present invention, the patient's genotype at nucleotide position +356 in intron 4 of EDN1 (rs2071942) is unknown. In certain embodiments, the patient may be determined to have an adenosine or a guanine at nucleotide position +356 in intron 4 of EDN1 (rs2071942).

In any method of the present invention, the patient's genotype at nucleotide position +61 in exon 5 of EDN1 (rs5370) may be known. Alternatively, in any method of the present invention, the patient's genotype at nucleotide position +61 in exon 5 of EDN1 (rs5370) is unknown. In any method of the present invention, the nucleotide at position +61 in exon 5 of EDN1 (rs5370) is part of a codon that encodes a lysine or an asparagine. In certain embodiments, the patient's genotype at nucleotide position +356 in intron 4 of EDN1 (rs2071942) and the patient's genotype at nucleotide position +61 in exon 5 of EDN1 (rs5370) are both unknown.

It is contemplated that in the context of the present invention, typically a medical practitioner (e.g., doctor, nurse, or their staff) will be evaluating whether to prescribe or administer a patient a β-adrenergic receptor targeting agent and in making that evaluation, the practitioner will order one or more tests regarding one or more of the patient's endothelin gene system member alleles or their encoded proteins. Accordingly, any method of the present invention may further comprise obtaining a patient history. For example, in methods wherein at least one polymorphism is at (i) nucleotide position +356 in intron 4 of EDN1 (rs2071942) or (ii) nucleotide position +61 in exon 5 of EDN1 (rs5370) encoding a polymorphism at amino acid 198 of EDN1 protein, wherein the individual is being considered for treatment with a β-adrenergic receptor targeting agent, a patient history regarding (i) or (ii) may be obtained. Any method of the present invention may further comprise preparing a report containing the results of determining (i) or (ii). Such a report may identify the patient by name, social security number, and/or other identification number or qualifier. It may also contain the actual data as a result of the determination or a summary of that data.

Other information may also be considered in determining whether a β-adrenergic receptor targeting agent is an appropriate drug for the patient. This may include race, gender, age, previous surgeries, heart failure stage, patient history regarding cardiovascular disease, diagnosis of other diseases or conditions, risks for other diseases or condition, drug allergies, drug toxicity, and/or other medications being taken.

In any method of the present invention, a biological sample may be obtained from a patient. Any biological sample may be obtained, such as one that contains DNA. A biological sample is a sample that contains biological material such as all or part of an organ, tissue, cells, nucleic acids, proteins, or other such macromolecules and substances. The sample may include sputum, serum, blood, plasma, spinal fluid, semen, lymphatic fluid, urine, stool, pleural effusion, ascites, a tissue sample, tissue biopsy, cell swab, or a combination thereof. In other embodiments of the invention, a sample may include cells that are from lung, skin, muscle, liver, renal, colon, prostate, breast, brain, bladder, small intestine, large intestine, cervix, stomach, pancreas, testes, ovaries, bone, marrow, or spine. In some embodiments, the sample is a whole blood, plasma or serum sample, while in other embodiments, the sample is obtained by lavage, smear, or swab of an area on or in the patient. In certain embodiments, the biological sample is a blood sample. In particular embodiments, a biological sample is blood, saliva, or skin.

To achieve certain methods of the present invention, a medical practitioner may obtain the biological sample for evaluation. The sample may be analyzed by the practitioner, or it may be sent to an outside or independent laboratory. The medical practitioner may or may not be cognizant of what information regarding the patient's endothelin gene system member(s) is being obtained. In any of these circumstances, the medical practitioner may consequently know the relevant information that will allow him or her to determine whether β-adrenergic receptor targeting agent therapy is an appropriate medicinal option. It is contemplated that, for example, a laboratory conducts the test to determine that patient's genotype such that its personnel also know the appropriate information. They may report back to the practitioner with the specific result of the test performed or the laboratory may simply report that a β-adrenergic receptor targeting agent is an appropriate drug based on the laboratory results.

It is contemplated that, in certain situations, a patient may be genotyped for one of these polymorphisms and then a subsequent determination is made with respect to the other polymorphism; in this scenario, two different samples may be evaluated. Alternatively, a single sample may be obtained and evaluated for two separate polymorphisms. Furthermore, it is contemplated that the invention also concerns performing a diplotype analysis or obtaining the results of a diplotype analysis.

In some embodiments of the invention, the sequence of a patient's endothelin gene system member and/or a protein encoded thereby may already have been evaluated. It is contemplated that this analysis may have been done prior to the patient being considered for treatment with a β-adrenergic receptor targeting agent or as part of a general examination. For example, the sequence of a patient's endothelin gene system member or a protein encoded thereby may be determined and entered into a database or entered into the patient's medical history. In this case, a medical practitioner may come to know what the sequence is by obtaining a patient history regarding the sequence at (i) nucleotide position +356 in intron 4 of EDN1 (rs2071942) or (ii) nucleotide position +61 in exon 5 of EDN1 (rs5370) encoding a polymorphism at amino acid 198 of EDN1 protein.

In particular embodiments, any method as described herein further comprises administering a β-adrenergic receptor targeting agent, such as bucindolol, to the patient after determining (i) the nucleotide position +356 in intron 4 of EDN1 (rs2071942) or (ii) the nucleotide position +61 in exon 5 of EDN1 (rs5370) encoding a polymorphism at amino acid 198 of EDN1 protein, wherein the patient has an adenosine or a guanine at nucleotide position +356 in intron 4 of EDN1 (rs2071942), and/or the nucleotide at position +61 in exon 5 of EDN1 (rs5370) encodes a lysine or an asparagine at amino acid 198 of EDN1 protein.

In particular embodiments, any method as described herein may further comprise administering to a patient a β-adrenergic receptor targeting agent that is not bucindolol after determining (i) the nucleotide position +356 in intron 4 of EDN1 (rs2071942) or (ii) the nucleotide position +61 in exon 5 of EDN1 (rs5370) encoding a polymorphism at amino acid 198 of EDN1 protein, wherein the patient has neither an adenosine or a guanine at nucleotide position +356 in intron 4 of EDN1 (rs2071942) nor a nucleotide at position +61 in exon 5 of EDN1 (rs5370) that encodes a lysine or an asparagine at amino acid 198 of EDN1 protein.

Other general aspects of the present invention contemplate a method for treating a patient with a heart condition comprising administering to the patient an effective amount of a β-adrenergic receptor targeting agent, wherein the patient has detectable EDN1 protein with an asparagine or lysine at amino acid 198 of EDN1 protein. The term "effective," as that term is used in the specification and/or claims (e.g., "an effective amount") means adequate to accomplish a desired, expected, or intended result. The β-adrenergic receptor targeting agent may be of any type described herein, such as a selective or a non-selective β-blocker. In particular embodiments, the β-adrenergic receptor targeting agent is bucindolol.

It is contemplated that not all of the patient's proteins will be evaluated in any embodiment of the invention but that a sample will be obtained and some of the proteins in the sample will be evaluated for their protein sequence. The same holds true for any evaluation of a patient's nucleic acids as well.

Another general aspect of the present invention contemplates a method for treating a patient with a heart condition comprising administering to the patient an effective amount of a β-adrenergic receptor targeting agent, wherein the patient does not have detectable EDN1 protein with an asparagine or lysine at amino acid 198 of EDN1 protein. The β-adrenergic receptor targeting agent may be of any type described herein, such as a selective or a non-selective β-blocker. In particular embodiments, the β-adrenergic receptor targeting agent is bucindolol.

Yet another general aspect of the present contemplates a method for treating a patient with a heart condition comprising administering to the patient an effective amount of a β-adrenergic receptor targeting agent, wherein the patient homozygous for an adenosine at nucleotide position +356 in intron 4 of EDN1 (rs2071942), or asparagine at amino acid 198 of EDN1 protein. Methods of the invention thus involve prescribing or administering a β-adrenergic receptor targeting agent to patients who are homozygous in this regard, regardless of how it is determined that the patient has that genotype. The β-adrenergic receptor targeting agent may be of any type described herein, such as a selective or a non-selective β-blocker. In particular embodiments, the β-adrenergic receptor targeting agent is bucindolol.

Other methods of the present invention contemplate a method for treating a patient with a β-adrenergic receptor targeting agent comprising: (a) determining (i) the presence or absence of a polymorphism at nucleotide position +356 in intron 4 of EDN1 (rs2071942) of the patient, and/or (ii) the presence or absence of a polymorphism at nucleotide position +61 in exon 5 of EDN1 (rs5370); and (b) either (i) prescribing a β-adrenergic receptor targeting agent for the patient, wherein the patient's genotype is homozygous for an adenosine at nucleotide position +356 in intron 4 of EDN1, or asparagine at amino acid 198 of EDN1 protein; or (ii) not prescribing a β-adrenergic receptor targeting agent for the patient, wherein the patient's genotype is not homozygous for an adenosine at nucleotide position +356 in intron 4 of EDN1 (rs2071942), or not an asparagine at amino acid 198 of EDN1 protein. The β-adrenergic receptor targeting agent may be of any type described herein, such as a selective or a non-selective β-blocker. In particular embodiments, the β-adrenergic receptor targeting agent is bucindolol.

In certain embodiments, a patient may be a non-Hispanic White or a non-Hispanic Black. Certain methods of the present invention comprise determining that a patient has an adenosine or a guanine at nucleotide position +356 in intron 4 of EDN1 (rs2071942), and the nucleotide at position +61 in exon 5 of EDN1 (rs5370) encodes a lysine or an asparagine at amino acid 198 of EDN1 protein. In certain embodiments of such methods, the patient is a non-Hispanic White.

The present invention also provides devices and compositions for the delivery of a β-adrenergic receptor targeting agent to an individual in need of such therapy. Additionally, methods may involve administering or prescribing other therapeutic agents or performing a surgical or other interventional strategy for treating the patient.

The embodiments discussed with respect to methods may be implemented in use of a β-adrenergic receptor targeting agent in the manufacture of a medicament.

The term "treatment" will be understood to refer to therapy with respect to a patient diagnosed with a medical condition, as described herein, or with symptoms of a medical condition, as opposed to preventative measures. However, as discussed above, preventative measures are also contemplated by the present invention.

Any embodiment discussed with respect to one aspect of the invention applies to other aspects of the invention as well. This includes embodiments discussed with respect to the endothelin gene system members described herein. For example, any embodiment discussed with respect to EDN1, EDN2, EDN3, EDNRA, EDNRB and ECE1 genes, alleles, or proteins may be implemented with respect to EDN1, EDN2, EDN3, EDNRA, EDNRB and ECE1 genes, alleles, or proteins, and vice versa.

The embodiments in the Examples section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. Partial sequence of genomic DNA for EDN1 based on Ensembl ENSG00000078401. The first SNP is rs2071942 in intervening sequence 4 (IVS-4), noted as [g/a]. The second SNP is rs5370 in exon 5, noted as [G/C]. Exons are in upper case; introns are in lower case. Exon 4 is underlined. Exon 5 is are all in capital letters (both underlined and not underlined). Primers are highlighted in gray.

DESCRIPTION OF ILLUSTRATIVE EMBODIMENTS

Figure 1:
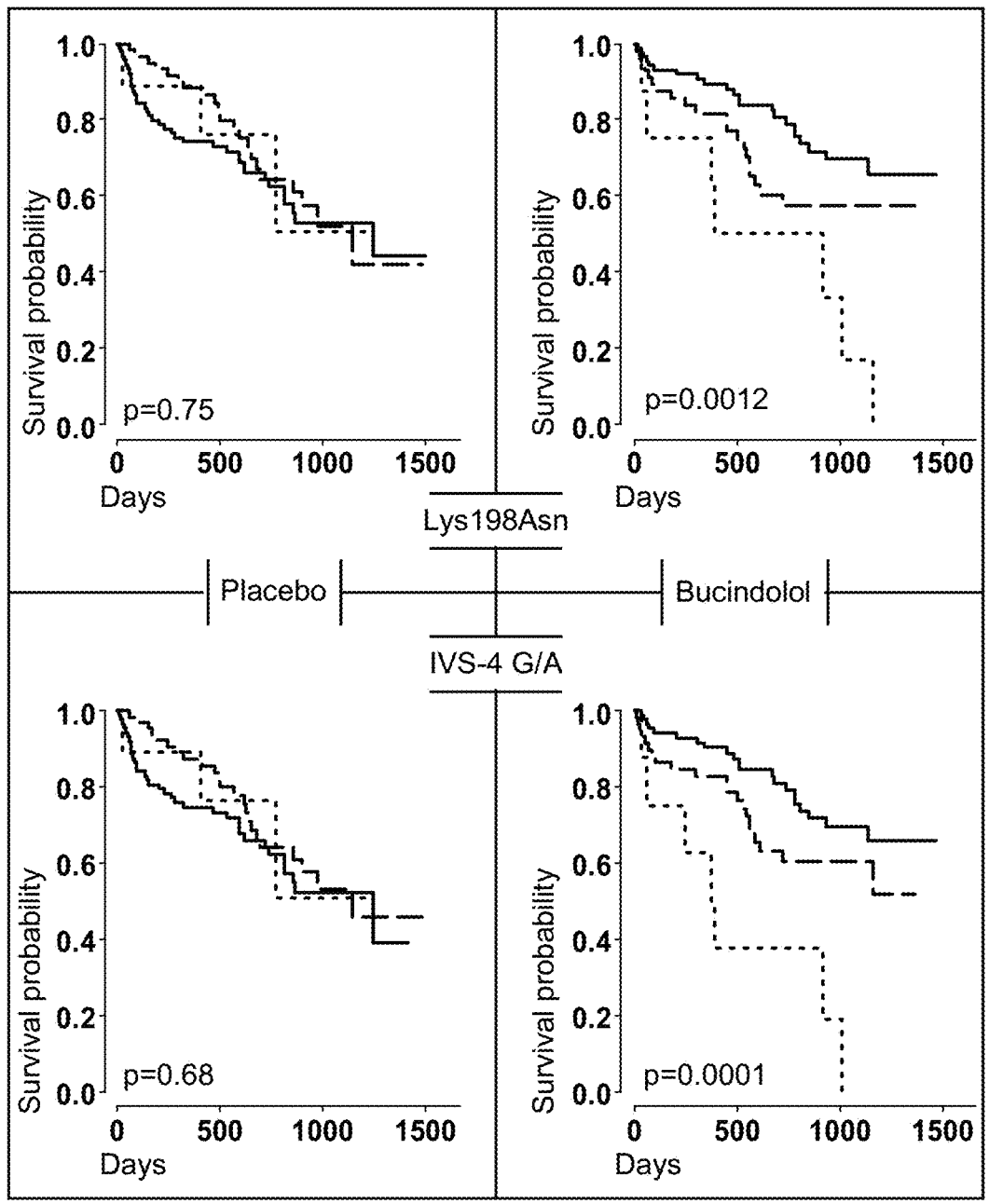
FIG. 1. Time to the combined event of first heart failure hospitalization or death for endothelin-1 polymorphisms Lys198Asn (top) and IVS-4 G/A by genotype. Common homozygotes, heterozygotes and rare homozygotes are depicted by the solid, dashed and dotted lines, respectively. The data are separated by treatment group with placebo treated and bucindolol treated subjects on the left and right, respectively. P-values are for the 2 df log-rank test. Event/number (for common homozygotes, heterozygotes and rare homozygotes, respectively) for Lys198Asn: (placebo: 36/89, 21/60, 3/9; bucindolol: 22/87, 20/55, 7/8) and IVS-G/A: (placebo: 35/87, 23/63, 3/9; Bucindolol: 21/84, 21/58, 7/8).
Figure 2:
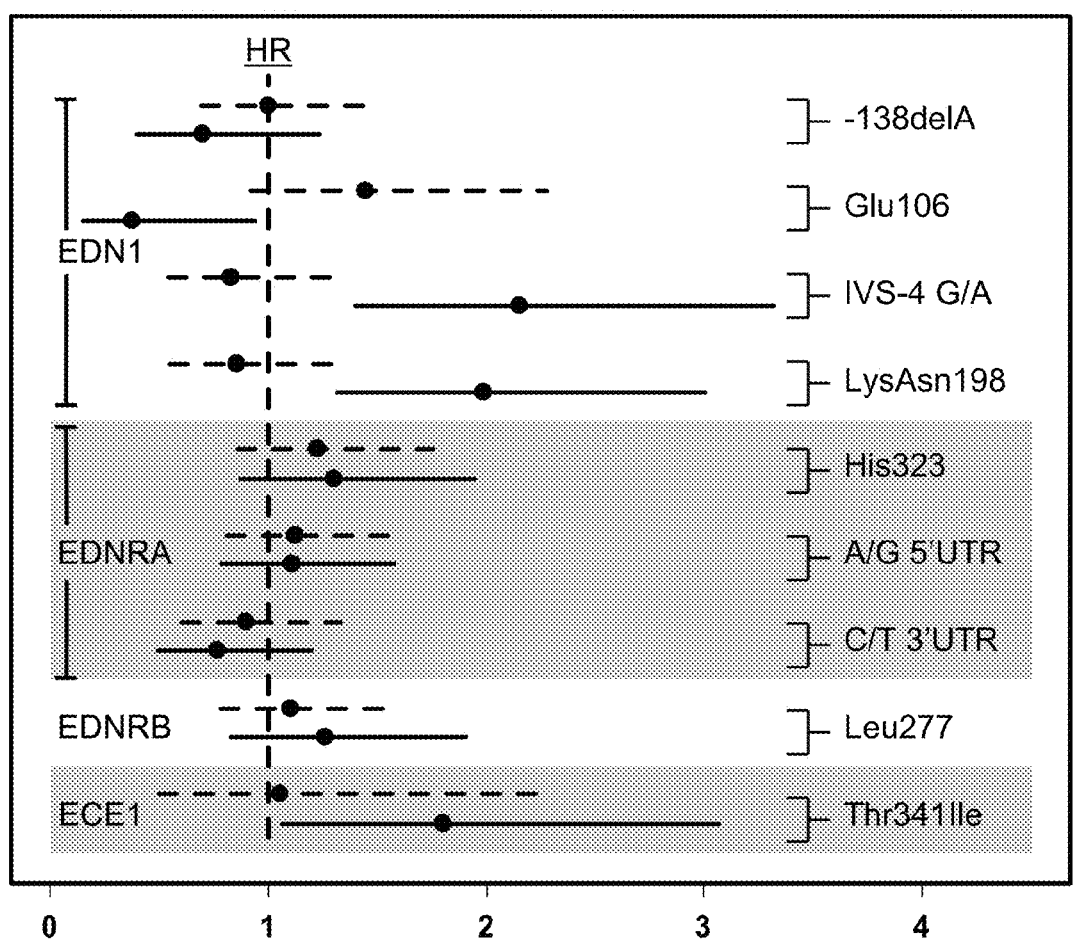
FIG. 2. Hazard ratios (HR) and 95% confidence intervals by treatment for the effect of a one-allele change in genotype, unadjusted for multiple comparisons for each endothelin system gene. EDN1-endothelin-1; EDNRA-endothelin receptor A; EDNRB-endothelin receptor B; ECE1-endothelin converting enzyme-1. Dashed and solid lines indicate the HRs for placebo and bucindolol groups, respectively. Values greater than one indicate greater risk associated with the less common allele.

As noted above, β-blocker therapy is standard treatment for a variety of medical conditions, such as cardiovascular conditions. Observed variation in response to medication is frequently mediated by genetic factors (Wilkinson, 2005; Evans and Relling, 2004; Weinshilboum, 2003). In the case of heart failure, the limited number of DNA banks established with large prospective trials has historically limited discovery of pharmacogenetic markers of drug response. More recently however, success in identifying pharmacogenetic predictors of drug response in heart failure have been reported (Liggett et al., 2006).

The endothelin gene system (EGS) is a candidate modifier pathway for heart failure (Nambi et al., 2001; Levin, 1995; Miyauchi and Masaki, 1999). Short endothelin peptides bind to endothelin receptors and are potent mediators of vasoconstriction, endothelial cell growth and vascular tone (Dzau, 1993; Yanagisawa et al., 1988). Changes in cardiac inotrophy and chronotrophy are mediated also through binding of endothelin to endothelin receptors A and B. Endothelin-1 is the predominant isoform expressed in the human heart and promotes cardiomyocyte contractility and hypertrophy (Yanagisawa et al., 1988; Inoue et al., 1989). Genetic variation in endothelin has been associated with blood pressure, left-ventricular hypertrophy and heart failure (Stevens and Brown, 1995; Vasku et al., 2002; Brugada et al., 1997). Moreover, biologically active endothelins interact with other 'neurohormonal' systems, including adrenergic and antiogensin systems, by pharmacologic crosstalk (Krum et al., 1996; Spieker et al., 2001; Spieker and Luscher, 2003; Giannessi et al., 2001).

Prior genetic studies of EGS single nucleotide polymorphisms (SNPs) focused on hypertension, arterial stiffness, vascular reactivity, arrhythmias, myocardial infarction, and heart failure (Iemitsu et al., 2006; Kozak et al., 2004; Jin et al., 2003; Iglarz et al., 2002; Tiret et al., 1999; Herrmann et al., 2001; Charron et al. 1999; Nicaud et al., 1999). The majority of these studies were not prospective and none of the known EGS polymorphisms have been tested for pharmacogenetic effects in heart failure. The present inventors hypothesized that response to β-blocker medication might be mediated by EGS variation. EGS SNPs were therefore studied for evidence of pharmacogenetic associations with clinical outcomes from a large, prospective, β-blocker heart failure trial reported previously (Beta-Blocker Evaluation of Survival Trial Investigators, 2001).

As shown in the Examples below, alleles at two EDN1 SNPs, Lys198Asn and G/A (IVS-4), commonly appearing in one of two complementary haplotypes, showed a strong pharmacogenetic interaction with β-adrenergic receptor targeting agent therapy on time to first heart failure hospitalization or all cause mortality. One result observed in these experiments is the novel identification of a haplotype associated with clinical response to a β-adrenergic receptor targeting agent in dilated cardiomyopathy—specifically, a β-blocker. The observed effect was confined to the treated group, with no significant effect in the placebo group, consistent with a true pharmacogenetic effect where drug 'exposure' elicits different outcomes based on the genetic background. A 'dose-response' trend by haplotype was observed, with subjects homozygous for the rare haplotype having the highest hazard ratios (HRs) as compared to the relative 'protective' effect of the common haplotype. A relative benefit of β-blocker therapy for the 56% of subjects homozygous for the common haplotype identifies a large subpopulation where β-blocker therapy appears most beneficial. Contrasted against this group are the 5.5% of subjects, homozygous for the rare complementary haplotype, for whom the combined endpoint hazard rate was almost three times greater on bucindolol than on placebo.

Bucindolol is a β-blocking agent with sympatholytic and vasodilator properties. Although it is not yet approved for clinical heart failure therapy, variation in outcomes in subpopulations of the study suggested to the inventors that underlying genetic differences may be responsible for observed differences in efficacy.

EDN1 G/A (IVS-4) and Lys198Asn are in tight linkage disequilibrium, which agrees with other published data and makes it impossible to distinguish which SNP is responsible for the observed effect. Strong linkage disequilibrium is also present between these SNPs and the rs1800543 variant in intron 3, which was not tested (Diefenbach et al., 2006). Genotyping of G/A IVS-4, Lys198Asn and rs1800543 largely define the same haplotype block extending from the beginning of intron 2 to exon 5. Three additional intronic SNPs not tested (rs:2070669, 1800543, 641347) and the Glu106 variant, which was not significant after multiple testing, also are contained in this haplotype block (Diefenbach et al., 2006).

Figure 3:
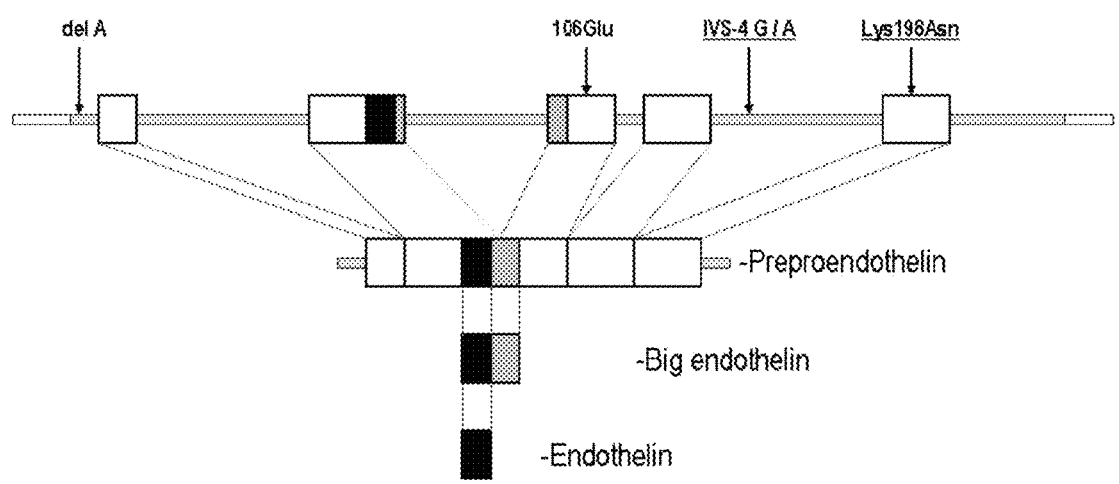
FIG. 3. Location of EDN1 polymorphisms studied. The genomic structure of the five exons (boxes) of the endothelin-1 gene is depicted (top) along with the four EDN1 polymorphisms analyzed. The Lys198Asn and IVS-4 G/A polymorphisms associated with bucindolol response are underlined. The Lys198Asn polymorphism is translated into the preproendothelin peptide, but is removed during processing into big endothelin.

The G/A (IVS-4) variant is at position +356 in intron 4 and does not localize to a known functional splicing or regulatory site (FIG. 3). It is located 6 base pairs downstream from an in silico predicted regulatory region using the ESPERR algorithm (Kolbe et al., 2004; King et al., 2005). The SNP does not alter splicing in an in silico model (GeneSplicer, world wide web at .tigr.org/), thus an obvious functional effect is lacking. Previous studies of this SNP showed a modest influence on variability of left ventricular hypertrophy 32 and double heterozygosity of IVS-4 G/A and rs1800997 predicted lower big endothelin levels in one study of chronic heart failure (Vasku et al., 2002). The highly linked rs1800543 also shows no predicted effect on splicing.

The nonsynonymous change at position 198 where a basic, charged lysine is replaced with a smaller, polar asparagine residue may affect secondary protein structure by extending regional coiled structure (GOR IV and PSIPRED algorithms: world wide web at npsa-pbil.ibcp.fr/ and bioinf.cs.ucl.ac.uk/, respectively). Serum endothelin-1 levels and big endothelin levels predict clinical heart failure phenotypes, and elevations correlate directly with heart failure severity and poorer prognosis and inversely with ejection fraction and cardiac index (Wei et al., 1994; McMurray et al. 1992; Hiroe et al., 1991). The differences in endothelin levels are mediated by levels of its precursor, big-endothelin (Wei et al., 1994). Without being bound by theory, the inventors suppose it is possible that the Asn198 variant subtly alters big-endothelin levels, stability, or conversion to endothelin-1 by endothelin converting enzyme (ECE). Compatible with this model are data from pregnant women and a separate hypertensive population where Asn198 alleles were predictive of higher serum endothelin levels (Tanaka et al., 2004; Barden et al., 2001).

Accordingly, the present invention, in part, concerns methods that utilize the genetic relationship between the polymorphisms at (i) nucleotide position +356 in intron 4 of EDN1 (rs2071942) or (ii) nucleotide position +61 in exon 5 of EDN1 (rs5370) encoding a polymorphism at amino acid 198 of EDN1 protein and β-adrenergic receptor targeting agent therapy.

I. ENDOTHELIN GENE SYSTEM MEMBERS

As mentioned above, endothelins bind to endothelin receptors and are potent mediators of vasoconstriction, endothelial cell growth and vascular tone. In a healthy individual, a delicate balance between vasoconstriction and vasodilation is maintained by endothelin, calcitonin and other vasoconstrictors on the one hand and nitric oxide, prostacyclin and other vasodilators on the other. Elevated activation of the endothelin signaling pathway also induces cell proliferation and/or survival and is implicated in a variety of malignancies (Zhang et al., 2006). A variety of endothelin gene system members and the proteins they encode are commercially available and/or have been prepared in the literature (e.g., Bachem AG, Switzerland; Invitrogen Corp., Carlsbad, Calif.; U.S. Pat. No. 6,066,502).

There are three isoforms of endothelin, each containing 21 amino acids: EDN1, EDN2 and EDN3. Two of the 21 amino acids differ between EDN1 and EDN2, and six between EDN1 and EDN3 (Inoue et al. 1989). Each endothelin is encoded by a separate preproendothelin, and each is subsequently produced via its own intermediate, referred to as big endothelin. The endothelins show varying regions of expression. Human EDN1 mRNA is found in several organs, including the brain, kidney, lung, uterus and placenta; human EDN2 mRNA is found abundantly in renal medulla and the jejunum, and plays a role in the ovulatory process (Ko et al., 2006); and human EDN3 mRNA is found abundantly in the jejunum and adrenal gland, as well as in the brain, spleen and renal medulla (Arinami et al., 1991).

It is necessary for a cell to express endothelin-converting enzyme (ECE) to catalyze the conversion of inactive forms of endothelins (163 amino acids) into bioactive endothelins (21 amino acids) to produce bioactive endothelins. There are at least two identified ECE genes, ECE1 and ECE2, and several isoforms of each have been detected. (Valdenaire et al., 1999; Meidan et al., 2005; Ikeda et al., 2002). ECE2 was discovered in 1995 as a novel member of the ECE1 gene family; the two gene products share 59% amino acid identity (Emoto and Yanagisawa, 1995; Turner et al., 2001).

Two key receptor types are known, EDNRA and EDNRB, which are G-protein-coupled receptors. EDNRA receptors are found in the smooth muscle tissue of blood vessels, and binding of endothelin to EDNRA increases vasoconstriction and the retention of sodium. These actions lead to increased blood pressure. EDNRB is primarily located on the endothelial cells that line the interior of the blood vessels. When endothelin binds to EDNRB receptors, this leads to increased natriuresis and diuresis and the release of nitric oxide (also endothelium-derived relaxing factor), all mechanisms that lower the blood pressure.

II. β-ADRENERGIC RECEPTOR TARGETING AGENTS

A. β-Adrenergic Receptors

The adrenergic receptors (AR) are a class of G protein-coupled receptors that are targets of the catecholamines. Adrenergic receptors specifically bind and are activated by their endogenous ligands, the catecholamines adrenaline and noradrenaline (also called epinephrine and norepinephrine, respectively). There are at least nine sub-types of adrenergic receptors (Dohlman et al., 1991; and Liggett et al., 1993), and they are typically categorized as α-adrenergic (e.g., $\alpha_1$, $\alpha_2$) or β-adrenergic (e.g., $\beta_1$, $\beta_2$ and $\beta_3$).

The $\beta_1$ adrenergic receptor ($\beta_1$-AR) is the principle subtype expressed on cardiac myocytes. The human heart expresses both the $\beta_1$-AR and the $\beta_2$-AR subtypes (Bristow et al, 1986; Bristow et al., 1988). Each receptor mediates positive inotropic and chronotropic responses to endogenous catecholamines and exogenously administered agonists (Bristow et al., 1986; Brodde et al., 1986; Brodde et al., 1992). $\beta_1$-AR triggers the heart's contractile response when activated, as it is by norepinephrine. In addition, the $\beta_1$ receptor has a central role in the progression of cardiomyopathy and other disease pathways. Increased activation of this receptor and its associated myopathic and arrhythmic pathways plays a major role in the natural history of heart failure. Once the cardiomyopathic process has begun, chronic $\beta_1$-adrenergic activation accelerates disease progression, as the failing heart tries to compensate for its impaired functioning by releasing more norepinephrine and increasing $\beta_1$-receptor signaling. The theory of β-receptor blockade rests in part on counteracting this cardiomyopathic pathway by blocking the $\beta_1$-receptor and reducing norepinephrine signaling.

$\beta_1$-AR has been cloned and sequenced (Frielle et al., 1987). The gene has been localized to chromosome q24-q26 of chromosome 10 (Yang-Feng et al., 1990). The human $\beta_1$AR has a deduced amino acid sequence of 477 amino acids.

The $\beta_2$ adrenergic receptor ($\beta_2$-AR) is found in the lung, smooth muscle, cerebellum and skeletal muscle. The receptor is involved in respiratory diseases such as chronic bronchitis, emphysema, acute respiratory distress syndrome and asthma. For example, in the lung, $\beta_2$-AR agonists cause bronchiole dilation and thus can be useful in the treatment of asthma. $\beta_2$-AR also promotes the release of insulin and is further responsible for relaxation of uterine muscle. Certain treatments of premature labor target $\beta_2$-AR. Other conditions associated with $\beta_2$-AR include hypertension, congestive heart failure and cardiovascular shock. $\beta_2$-AR agonists may also be useful for treatment of neurological disorders.

The gene encoding the human $\beta_2$-AR has also been cloned and sequenced (Kobilka et al., 1987). It is an intronless gene that has been localized to q31-q32 of chromosome 5. The deduced amino acid sequence consists of 413 amino acids, with seven clusters of hydrophobic residues thought to represent transmembrane spanning domains. The N-terminus is extracellular, containing two sites for asparagine-linked glycosylation. The transmembrane spanning domains are connected by three extracellular and three intracellular loops. The C-terminus is intracellular.

$\beta_3$-AR is less well characterized as $\beta_1$-AR and $\beta_2$-AR. This receptor contains 402 amino acids and is capable of activating adenylate cyclase in the presence of an agonist. Through a pharmacological comparison of the activation of adenylate cyclase in the presence of agonists and the reaction towards different antagonists, this receptor was shown to differ from $\beta_1$-AR and $\beta_2$-AR. The expression of $\beta_3$-AR has been reported in various tissues such as adipose tissue and tissues of the digestive tract (esophagus, colon and gallbladder) (Bond et al., 1988); Coleman et al., 1987); Bianchetti et al., 1990); Granneman et al., 1991). $\beta_3$-AR agonists have been pursued as antiobesity and antidiabetic agents, and may also find in controlling the frequent urge of urination (see U.S. Patent Publication No. 2003/0176412). The cloning and initial sequencing of the human and mouse $\beta_3$-AR genes have been previously described (Nahmias et al., 1991; Emorine et al., 1989).

B. β-Adrenergic Receptor Targeting Agents

β-blockers are a class of drugs used for various indications, but particularly for the management of cardiac arrhythmias and cardioprotection after myocardial infarction. Although β-blockers were once contraindicated in congestive heart failure, as they have the potential to worsen the condition, studies in the late 1990s showed their positive effects on morbidity and mortality in congestive heart failure (Hjalmarson et al., 2000; Leizorovicz et al., 2002; Packer et al., 2002). Although no β-blocker is approved for anxiolytic use by the U.S. Food and Drug Administration, some people use β-blockers to avoid stage fright and tremor during public performance and auditions. Indeed, some Olympic marksmen take β-blockers to provide more aiming time between heart beats since these drugs lower one's heart rate. Presently, more than ten different β-blockers are available, all by prescription.

Acting as antagonists of β-adrenergic receptors, β-blockers block the action of endogenous catecholamines (epinephrine (adrenaline) and norepinephrine (noradrenaline), in particular) on β-adrenergic receptors, part of the sympathetic nervous system that mediates the "fight or flight" response. This action slows the nerve impulses that travel through the heart. As a result, the heart beats more slowly and less strongly, and blood pressure falls. β-blockers also block impulses that can cause arrhythmia, and stop blood vessels around the brain from widening so easily, helping to prevent migraines.

Non-limiting examples of a β-blockers include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the β-blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

In certain aspects, "derivative" refers to a chemically modified compound that still retains the desired effects of the compound prior to the chemical modification. Such derivatives may have the addition, removal, or substitution of one or more chemical moieties on the parent molecule. Non-limiting examples of the types modifications that can be made to the compounds and structures disclosed herein include the addition or removal of lower alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom to generate, for example, a heterocycloalkyl structure. The present invention specifically contemplates employing β-adrenergic receptor targeting agent derivatives in the methods described herein.

As agents that target β-adrenergic receptors, the present invention contemplates all categories of β-blockers, including selective and non-selective β-blockers. Such agents are typically commercially available. The present invention also specifically contemplates β-blockers that have yet to be developed.

β-blockers that affect both $β_1$- and $β_2$-adrenergic receptors are termed "non-selective β-blockers." Non-limiting examples of non-selective β-blockers that may be employed in the present invention include alprenolol, bucindolol, carteolol, carvedilol, labetalol, levobunol, mepindolol, metipranolol, nadolol, oxprenolol, penbutolol, pindolol, prebutolol sulfate, propanolol, sotalol, rimolol and timolol.

"Selective β-blockers" primarily affect $β_1$ receptors. Selective β-blockers gradually become less selective at higher doses. Non-limiting examples of selective β-blockers that may be employed in the present invention include acebutolol, atenolol, betaxolol, hydrochloride, bisoprolol, celiprolol, esmolol, metaprolol, metoprolol, nebivolol and timolol.

III. ANALYSIS OF POLYMORPHISMS

Certain genetic variants of the present invention are in coding regions of endothelin gene system members and therefore typically affect the encoded proteins; as such, the presence of a endothelin gene system member polymorphism can be determined from either the sequence of the nucleic acid or the protein. However, not every polymorphism in a gene results in a difference in the encoded protein: for example, the G/A (IVS-4) polymorphism described herein does not the sequence of a protein. The terms "endothelin gene system member polymorphism," therefore, is a term of art and refers to polymorphisms in the nucleic acid or amino acid sequence of a endothelin gene system member gene or gene product. A variety of different methodologies can be employed for the purpose of detecting polymorphisms in genes or gene products.

A. Nucleic Acids

Certain embodiments of the present invention concern various nucleic acids, including amplification primers, oligonucleotide probes, and other nucleic acid elements involved in the analysis of genomic DNA. In certain aspects, a nucleic acid comprises a wild-type, a mutant, or a polymorphic nucleic acid.

For the purposes of identifying the location of a polymorphism, the first nucleotide of the start codon of the coding region (the adenine of the ATG in a DNA molecule and the adenine of the AUG in an RNA molecule) of an endothelin gene system member is considered nucleotide "1" and the numbers progress according along the coding sequence. Similarly, the first amino acid of the translated protein product (the methionine) is considered amino acid "1."

The term "nucleic acid" is well known in the art. A "nucleic acid" as used herein will generally refer to a molecule (i.e., a strand) of DNA or RNA comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product.

In some embodiments, nucleic acids of the invention comprise or are complementary to all or 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1165, 1200, 1300, 1400, 1500 or more contiguous nucleotides, or any range derivable therein, of an endothelin gene system member cDNA sequence comprising a polymorphism as described herein. One of skill in the art knows how to design and use primers and probes for hybridization and amplification, including the limits of homology needed to implement primers and probes.

These definitions generally refer to a single-stranded molecule, but in specific embodiments will also encompass an additional strand that is partially, substantially, or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

In particular aspects, a nucleic acid encodes a protein, polypeptide, or peptide. In certain embodiments, the present invention concerns novel compositions comprising at least one proteinaceous molecule. As used herein, a "proteinaceous molecule," "proteinaceous composition," "proteinaceous compound," "proteinaceous chain," or "proteinaceous material" generally refers, but is not limited to, a protein of greater than about 20 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

1. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

2. Purification of Nucleic Acids

A nucleic acid may be purified on polyacrylamide gels, cesium chloride centrifugation gradients, chromatography columns or by any other means known to one of ordinary skill in the art (see for example, Sambrook et al., 2001, incorporated herein by reference). In some aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

3. Nucleic Acid Segments

In certain embodiments, the nucleic acid is a nucleic acid segment. As used herein, the term "nucleic acid segment," are fragments of a nucleic acid, such as, for a non-limiting example, those that encode only part of an endothelin gene system member locus or gene sequence. Thus, a "nucleic acid segment" may comprise any part of a gene sequence, including from about 2 nucleotides to the full length gene including promoter regions to the polyadenylation signal and any length that includes all the coding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

4. Nucleic Acid Complements

The present invention also encompasses a nucleic acid that is complementary to a nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule. In preferred embodiments, a complement is a hybridization probe or amplification primer for the detection of a nucleic acid polymorphism.

As used herein, the term "complementary" or "complement" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some diagnostic or detection embodiments, completely complementary nucleic acids are preferred.

5. Nucleic Acid Detection and Evaluation

Genotyping may be performed using methods as described in Example 1 below, or as previously described in Small et al. (2002), which is incorporated herein by reference. It will be understood by the skilled artisan that other standard techniques are available for genotyping and any technique may be used with the present invention. General methods of nucleic acid detection methods are provided below, followed by specific examples employed for the identification of polymorphisms, including single nucleotide polymorphisms (SNPs).

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense or coding) strand of a nucleic acid molecule is also intended to include the thymine (uridine), adenine, guanine, or cytosine (respectively) at the corresponding site on a minus (antisense or noncoding) strand of a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to the sense strand, only for the purpose of convenience.

A nucleic acid mixture may be isolated from a biological sample taken from the individual, such as a blood sample or tissue sample, or any biological sample discussed herein, using standard techniques such as disclosed in Jones (1963) which is hereby incorporated by reference. The nucleic acid mixture may be comprised of genomic DNA, mRNA, or cDNA and, in the latter two cases, the biological sample must be obtained from an organ in which an endothelin gene system member is expressed. Furthermore it will be understood by the skilled artisan that mRNA or cDNA preparations would not be used to detect polymorphisms located in introns or in 5' and 3' nontranscribed regions.

The ability to predict a patient's response to a β-adrenergic receptor targeting agent is useful for physicians in making decisions about how to treat a patient having heart failure. A patient whose genotype indicates the patient will probably respond well to the agent would be a better candidate for β-adrenergic receptor targeting agent therapy than a patient who is likely to exhibit an intermediate response or no response, and the physician would be able to determine with less trial and error which individuals should receive an alternative form of therapy.

In the genotyping methods used in the present invention, the identity of a nucleotide (or nucleotide pair) at a polymorphic site may be determined by amplifying a target region(s) containing the polymorphic site(s) directly from one or both copies of a β-adrenergic receptor targeting agent gene present in the individual and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

The target region(s) may be amplified using any oligonucleotide-directed amplification method, including but not limited to polymerase chain reaction (PCR) (U.S. Pat. No. 4,965,188), ligase chain reaction (LCR) (Barany et al., 1991; WO90/01069), and oligonucleotide ligation assay (OLA) (Landegren et al., 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker et al., 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes and beads. The solid support may be treated, coated or derivatized to facilitate the immobilization of the allele-specific oligonucleotide or target nucleic acid.

The genotype for one or more polymorphic sites in an endothelin gene system member of an individual may also be determined by hybridization of one or both copies of the gene, or a fragment thereof, to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., 1985; Meyers et al., 1985) and proteins which recognize nucleotide mismatches, such as the E. coli mutS protein (Modrich, 1991). Alternatively, variant alleles can be identified by single strand conformation polymorphism (SSCP) analysis (Orita et al., 1989; Humphries et al., 1996) or denaturing gradient gel electrophoresis (DGGE) (Wartell et al., 1990; Sheffield et al., 1989).

A polymerase-mediated primer extension method may also be used to identify the polymorphism(s). Several such methods have been described in the patent and scientific literature. Extended primers containing a polymorphism may be detected by mass spectrometry as described in U.S. Pat. No. 5,605,798. An other primer extension method is allele-specific PCR (Ruano et al., 1989); Ruano et al., 1991; WO 93/22456; Turki et al., 1995).

Polymorphic variations in endothelin gene system members can also be detected using differential digestion of DNA by certain restriction enzymes (Small et al., 2002) or by any other method that identifies polymorphisms.

a. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M $NaHPO_4$, 7% sodium dodecyl sulfate (SDS), 1 mM EDTA at 65° C., and washing in 0.1×SSC/0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

b. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the endothelin gene system member gene locus, or variants thereof, and fragments thereof are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329,822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

c. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

d. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

e. Specific Examples of Polymorphism Nucleic Acid Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are been widely used in human and animal genetic analyses.

Another class of polymorphisms are generated by the replacement of a single nucleotide. Such single nucleotide polymorphisms (SNPs) rarely result in changes in a restriction endonuclease site. Thus, SNPs are rarely detectable restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset Alzheimer's disease etc.

Several methods have been developed to screen polymorphisms and some examples are listed below. The reference of Kwok and Chen (2003) and Kwok (2001) provide overviews of some of these methods; both of these references are specifically incorporated by reference.

SNPs relating to endothelin gene system members can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

i. DNA Sequencing

The most commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes (Mullis et al., 1986; European Patent Application 50,424; European Patent Application. 84,796, European Patent Application 258,017, European Patent Application. 237,362; European Patent Application. 201,184; U.S. Pat. Nos. 4,683,202; 4,582,788; and 4,683,194), all of the above incorporated herein by reference.

ii. Exonuclease Resistance

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

iii. Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

iv. Extension in Solution

French Patent 2,650,840 and PCT Application WO91/02087 discuss a solution-based method for determining the identity of the nucleotide of a polymorphic site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

v. Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

vi. Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here PCR is used to achieve the exponential amplification of target DNA, which is then detected using the OLA.

vii. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

viii. Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected. See Lu et al., 2004.

In some cases, the assay is conducted on a solid-surface or in an array format.

ix. Other Methods to Detect SNPs

Several other specific methods for polymorphism detection and identification are presented below and may be used as such or with suitable modifications in conjunction with identifying polymorphisms of endothelin gene system members in the present invention. Several other methods are also described on the SNP web site of the NCBI on the world wide web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter is referred to as "haplotype tag SNPs (htSNPs)," markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to variant detector array (VDA) can be performed by a Affymetrix High Throughput Screening Center and analyzed with computerized software.

A method called Chip Assay uses PCR amplification of genomic segments by standard or long PCR protocols. Hybridization products are analyzed by VDA, Halushka et al. (1999), incorporated herein by reference. SNPs are generally classified as "Certain" or "Likely" based on computer analysis of hybridization patterns. By comparison to alternative detection methods such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using the following conditions: 200 ng DNA template, 0.5 µM each primer, 80 µM each of dCTP, dATP, dTTP and dGTP, 5% formamide, 1.5 mM $MgCl_2$, 0.5 U of Taq polymerase and 0.1 volume of the Taq buffer. Thermal cycling is performed and resulting PCR-products are analyzed by PCR-single strand conformation polymorphism (PCR-SSCP) analysis, under a variety of conditions, e.g, 5 or 10% polyacrylamide gel with 15% urea, with or without 5% glycerol. Electrophoresis is performed overnight. PCR-products that show mobility shifts are reamplified and sequenced to identify nucleotide variation.

In a method called CGAP-GAI (DEMIGLACE), sequence and alignment data (from a PHRAP.ace file), quality scores for the sequence base calls (from PHRED quality files), distance information (from PHYLIP dnadist and neighbour programs) and base-calling data (from PHRED "-d" switch) are loaded into memory. Sequences are aligned and examined for each vertical chunk ('slice') of the resulting assembly for disagreement. Any such slice is considered a candidate SNP (DEMIGLACE). A number of filters are used by DEMIGLACE to eliminate slices that are not likely to represent true polymorphisms. These include filters that: (i) exclude sequences in any given slice from SNP consideration where neighboring sequence quality scores drop 40% or more; (ii) exclude calls in which peak amplitude is below the fifteenth percentile of all base calls for that nucleotide type; (iii) disqualify regions of a sequence having a high number of disagreements with the consensus from participating in SNP calculations; (iv) removed from consideration any base call with an alternative call in which the peak takes up 25% or more of the area of the called peak; (v) exclude variations that occur in only one read direction. PHRED quality scores were converted into probability-of-error values for each nucleotide in the slice. Standard Baysian methods are used to calculate the posterior probability that there is evidence of nucleotide heterogeneity at a given location.

In a method called CU-RDF (RESEQ), PCR amplification is performed from DNA isolated from blood using specific primers for each SNP, and after typical cleanup protocols to remove unused primers and free nucleotides, direct sequencing using the same or nested primers.

In a method called DEBNICK (METHOD-B), a comparative analysis of clustered EST sequences is performed and confirmed by fluorescent-based DNA sequencing. In a related method, called DEBNICK (METHOD-C), comparative analysis of clustered EST sequences with phred quality >20 at the site of the mismatch, average phred quality >=20 over 5 bases 5'-FLANK and 3' to the SNP, no mismatches in 5 bases 5' and 3' to the SNP, at least two occurrences of each allele is performed and confirmed by examining traces.

In a method identified by ERO (RESEQ), new primers sets are designed for electronically published STSs and used to amplify DNA from 10 different mouse strains. The amplification product from each strain is then gel purified and sequenced using a standard dideoxy, cycle sequencing technique with $^{33}$P-labeled terminators. All the ddATP terminated reactions are then loaded in adjacent lanes of a sequencing gel followed by all of the ddGTP reactions and so on. SNPs are identified by visually scanning the radiographs.

In another method identified as ERO (RESEQ-HT), new primers sets are designed for electronically published murine DNA sequences and used to amplify DNA from 10 different mouse strains. The amplification product from each strain is prepared for sequencing by treating with Exonuclease I and Shrimp Alkaline Phosphatase. Sequencing is performed using ABI Prism Big Dye Terminator Ready Reaction Kit (Perkin-Elmer) and sequence samples are run on the 3700 DNA Analyzer (96 Capillary Sequencer).

FGU-CBT (SCA2-SNP) identifies a method where the region containing the SNP were PCR amplified using the primers SCA2-FP3 and SCA2-RP3. Approximately 100 ng of genomic DNA is amplified in a 50 ml reaction volume containing a final concentration of 5 mM Tris, 25 mM KCl, 0.75 mM $MgCl_2$, 0.05% gelatin, 20 pmol of each primer and 0.5 U of Taq DNA polymerase. Samples are denatured, annealed and extended and the PCR product is purified from a band cut out of the agarose gel using, for example, the QIAquick gel extraction kit (Qiagen) and is sequenced using dye terminator chemistry on an ABI Prism 377 automated DNA sequencer with the PCR primers.

In a method identified as JBLACK (SEQ/RESTRICT), two independent PCR reactions are performed with genomic DNA. Products from the first reaction are analyzed by sequencing, indicating a unique FspI restriction site. The mutation is confirmed in the product of the second PCR reaction by digesting with Fsp I.

In a method described as KWOK(1), SNPs are identified by comparing high quality genomic sequence data from four randomly chosen individuals by direct DNA sequencing of PCR products with dye-terminator chemistry (see Kwok et al., 1996). In a related method identified as KWOK(2) SNPs are identified by comparing high quality genomic sequence data from overlapping large-insert clones such as bacterial artificial chromosomes (BACs) or P1-based artificial chromosomes (PACs). An STS containing this SNP is then developed and the existence of the SNP in various populations is confirmed by pooled DNA sequencing (see Taillon-Miller et al., 1998). In another similar method called KWOK (3), SNPs are identified by comparing high quality genomic sequence data from overlapping large-insert clones BACs or PACs. The SNPs found by this approach represent DNA sequence variations between the two donor chromosomes but the allele frequencies in the general population have not yet been determined. In method KWOK(5), SNPs are identified by comparing high quality genomic sequence data from a homozygous DNA sample and one or more pooled DNA samples by direct DNA sequencing of PCR products with dye-terminator chemistry. The STSs used are developed from sequence data found in publicly available databases. Specifically, these STSs are amplified by PCR against a complete hydatidiform mole (CHM) that has been shown to be homozygous at all loci and a pool of DNA samples from 80 CEPH parents (see Kwok et al., 1994).

In another such method, KWOK (OverlapSnpDetectionWithPolyBayes), SNPs are discovered by automated computer analysis of overlapping regions of large-insert human genomic clone sequences. For data acquisition, clone sequences are obtained directly from large-scale sequencing centers. This is necessary because base quality sequences are not present/available through GenBank. Raw data processing involves analyzed of clone sequences and accompanying base quality information for consistency. Finished ('base perfect', error rate lower than 1 in 10,000 bp) sequences with no associated base quality sequences are assigned a uniform base quality value of 40 (1 in 10,000 bp error rate). Draft sequences without base quality values are rejected. Processed sequences are entered into a local database. A version of each sequence with known human repeats masked is also stored. Repeat masking is performed with the program "MASKERAID." Overlap detection: Putative overlaps are detected with the program "WUBLAST." Several filtering steps followed in order to eliminate false overlap detection results, i.e. similarities between a pair of clone sequences that arise due to sequence duplication as opposed to true overlap. Total length of overlap, overall percent similarity, number of sequence differences between nucleotides with high base quality value "high-quality mismatches." Results are also compared to results of restriction fragment mapping of genomic clones at Washington University Genome Sequencing Center, finisher's reports on overlaps, and results of the sequence contig building effort at the NCBI. SNP detection: Overlapping pairs of clone sequence are analyzed for candidate SNP sites with the 'POLYBAYES' SNP detection software. Sequence differences between the pair of sequences are scored for the probability of representing true sequence variation as opposed to sequencing error. This process requires the presence of base quality values for both sequences. High-scoring candidates are extracted. The search is restricted to substitution-type single base pair variations. Confidence score of candidate SNP is computed by the POLYBAYES software.

In method identified by KWOK (TaqMan assay), the TaqMan assay is used to determine genotypes for 90 random individuals. In method identified by KYUGEN(Q1), DNA samples of indicated populations are pooled and analyzed by PLACE-SSCP. Peak heights of each allele in the pooled analysis are corrected by those in a heterozygote, and are subsequently used for calculation of allele frequencies. Allele frequencies higher than 10% are reliably quantified by this method. Allele frequency=0 (zero) means that the allele was found among individuals, but the corresponding peak is not seen in the examination of pool. Allele frequency=0-0.1 indicates that minor alleles are detected in the pool but the peaks are too low to reliably quantify.

In yet another method identified as KYUGEN (Method 1), PCR products are post-labeled with fluorescent dyes and analyzed by an automated capillary electrophoresis system under SSCP conditions (PLACE-SSCP). Four or more individual DNAs are analyzed with or without two pooled DNA (Japanese pool and CEPH parents pool) in a series of experiments. Alleles are identified by visual inspection. Individual DNAs with different genotypes are sequenced and SNPs identified. Allele frequencies are estimated from peak heights in the pooled samples after correction of signal bias using peak heights in heterozygotes. For the PCR primers are tagged to have 5'-ATT or 5'-GTT at their ends for post-labeling of both strands. Samples of DNA (10 ng/ul) are amplified in reaction mixtures containing the buffer (10 mM Tris-HCl, pH 8.3 or 9.3, 50 mM KCl, 2.0 mM $MgCl_2$), 0.25 µM of each primer, 200 µM of each dNTP, and 0.025 units/µl of Taq DNA polymerase premixed with anti-Taq antibody. The two strands of PCR products are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. For the SSCP: an aliquot of fluorescently labeled PCR products and TAMRA-labeled internal markers are added to deionized formamide, and denatured. Electrophoresis is performed in a capillary using an ABI Prism 310 Genetic Analyzer. Genescan softwares (P-E Biosystems) are used for data collection and data processing. DNA of individuals (two to eleven) including those who showed different genotypes on SSCP are subjected for direct sequencing using big-dye terminator chemistry, on ABI Prism 310 sequencers. Multiple sequence trace files obtained from ABI Prism 310 are processed and aligned by Phred/Phrap and viewed using Consed viewer. SNPs are identified by PolyPhred software and visual inspection.

In yet another method identified as KYUGEN (Method 2), individuals with different genotypes are searched by denaturing HPLC (DHPLC) or PLACE-SSCP (Inazuka et al., 1997) and their sequences are determined to identify SNPs. PCR is performed with primers tagged with 5'-ATT or 5'-GTT at their ends for post-labeling of both strands. DHPLC analysis is carried out using the WAVE DNA fragment analysis system (Transgenomic). PCR products are injected into DNASep column, and separated under the conditions determined using WAVEMaker program (Transgenomic). The two strands of PCR products that are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. SSCP followed by electrophoresis is performed in a capillary using an ABI Prism 310 Genetic Analyzer. Genescan softwares (P-E Biosystems). DNA of individuals including those who showed different genotypes on DHPLC or SSCP are subjected for direct sequencing using big-dye terminator chemistry, on ABI Prism 310 sequencer. Multiple sequence trace files obtained from ABI Prism 310 are processed and aligned by Phred/Phrap and viewed using Consed viewer. SNPs are identified by PolyPhred software and visual inspection. Trace chromatogram data of EST sequences in Unigene are processed with PHRED. To identify likely SNPs, single base mismatches are reported from multiple sequence alignments produced by the programs PHRAP, BRO and POA for each Unigene cluster. BRO corrected possible misreported EST orientations, while POA identified and analyzed non-linear alignment structures indicative of gene mixing/chimeras that might produce spurious SNPs. Bayesian inference is used to weigh evidence for true polymorphism versus sequencing error, misalignment or ambiguity, misclustering or chimeric EST sequences, assessing data such as raw chromatogram height, sharpness, overlap and spacing; sequencing error rates; context-sensitivity; cDNA library origin, etc.

In method identified as MARSHFIELD (Method-B), overlapping human DNA sequences which contained putative insertion/deletion polymorphisms are identified through searches of public databases. PCR primers which flanked each polymorphic site are selected from the consensus sequences. Primers are used to amplify individual or pooled human genomic DNA. Resulting PCR products are resolved on a denaturing polyacrylamide gel and a PhosphorImager is used to estimate allele frequencies from DNA pools.

f. Linkage Disequilibrium

Polymorphisms in linkage disequilibrium with another polymorphism in which identification of one polymorphism is predictive of the identity of the linked polymorphism. "Linkage disequilibrium" ("LD" as used herein, though also referred to as "LED" in the art) refers to a situation where a particular combination of alleles (i.e., a variant form of a given gene) or polymorphisms at two loci appears more frequently than would be expected by chance. "Significant" as used in respect to linkage disequilibrium, as determined by one of skill in the art, is contemplated to be a statistical p or a value that may be 0.25 or 0.1 and may be 0.1, 0.05, 0.001, 0.00001, or less. The polymorphism at position 198 of EDN1 protein may be determined by evaluating a polymorphism in linkage disequilibrium therewith. The invention may be implemented in this manner with respect to one or more polymorphisms so as to allow haplotype analysis. "Haplotype" is used according to its plain and ordinary meaning to one skilled in the art. It refers to a collective genotype of two or more alleles or polymorphisms along one of the homologous chromosomes.

g. Pyrosequencing

Pyrosequencing is a method of DNA sequencing based on a "sequencing by synthesis" principle. Polymorphisms may be detected using pyrosequencing, and certain embodiments of the present invention employ this method. The method is based on a chemical light-producing enzymatic reaction that is triggered when a molecular recognition event occurs. Simply put, the method allows sequencing of a single strand of DNA by synthesizing the complementary strand along it. Each time a nucleotide is incorporated into the growing chain, a cascade of enzymatic reactions is triggered which results in a light signal.

More specifically, pyrosequencing is based on the detection of inorganic pyrophosphates (PPi) released during a polymerase reaction. A sequencing primer is first hybridized to a single stranded DNA template and incubated with a DNA polymerase. In addition to the polymerase, the enzymes ATP sulfurylase, luciferase, and apyrase are added to the reaction along with the substrates, adenine 5' phosphosulfate (APS) and luciferin. Subsequently, individual nucleotides are added. When an added nucleotide is complementary to the next available base in the template strand, it is incorporated into the extension product, releasing pyrophosphate. In the presence of adenosine 5' phorphosulfate, pyrophosphate is converted into ATP by apyrase in a quantity equimolar to the amount of incorporated nucleotide. The ATP generated by the reaction with apyrase then drives the luciferase-mediated conversion of luciferin to oxyluciferin, generating visible light in amounts that are proportional to the amount of ATP, and thus the number of nucleotides incorporated into the growing DNA template. The light produced by the luciferase-catalyzed reaction may be detected by, for example, a charge coupled device (CCD) camera.

B. Evaluating the Protein

Alternatively, polymorphic variation can be determined by any method that detects an amino acid variation at a particular position, such as at position 198 of EDN1 protein. The invention should not be limited by any particular method for achieving this. For example, a sample of fluid or tissue may be obtained from an individual and the amino acid at position 198 of EDN1 protein is determined. Such detection can be by various methods including antibody based assays (Western blots, ELISA) or amino acid analysis (high pressure liquid chromatography or mass spectroscopy) could be used that would detect whether the protein has Lys or Asn.

Therefore, in certain embodiments, the present invention concerns compositions comprising at least one proteinaceous molecule, such as a protein encoded by an endothelin gene system member, or an protein that binds thereto, such as an antibody. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (world wide web at .ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

1. Protein Purification

It may be desirable to purify an endothelin gene system member from a sample or purify a protein that binds endothelin gene system member, such as an antibody. Such techniques are widely employed and the invention is not intended to be limited with respect to protein purification. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention may concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "–fold purification number." The actual units used to represent the amount of activity will, of course, be dependent upon the particular assay technique chosen to follow the purification and whether or not the expressed protein or peptide exhibits a detectable activity.

A variety of techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "–fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

2. Antibodies

Another embodiment of the present invention are antibodies, in some cases, a human monoclonal antibody immunoreactive with the polypeptide sequence of an endothelin gene system member. It is understood that antibodies can be used for detecting an endothelin gene system member, particularly an endothelin gene system member that is the result of a particular polymorphism. It is contemplated that antibodies particularly useful in the context of the present invention are those that differentially bind EDN1 protein protein with a lysine or an asparagine at amino acid 198 so as to distinguish between the two populations.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (see, e.g., Harlow and Lane, 1988; incorporated herein by reference).

a. Antibody Generation

In certain embodiments, the present invention involves antibodies. For example, all or part of a monoclonal may be used in determining the amino acid at position 389. As detailed above, in addition to antibodies generated against full length proteins, antibodies also may be generated in response to smaller constructs comprising epitopic core regions, including wild-type and mutant epitopes. The techniques for preparing and using various antibody-based constructs and fragments are well known in the art. Means for preparing and characterizing antibodies are also well known in the art (See, e.g., Harlow and Lane, 1988; incorporated herein by reference).

Monoclonal antibodies (mAbs) are recognized to have certain advantages, e.g., reproducibility and large-scale production, and their use is generally preferred. The invention thus provides monoclonal antibodies of the human, murine, monkey, rat, hamster, rabbit and even chicken origin.

The methods for generating monoclonal antibodies (mAbs) generally begin along the same lines as those for preparing polyclonal antibodies. Briefly, a polyclonal antibody may be prepared by immunizing an animal with an immunogenic polypeptide composition in accordance with the present invention and collecting antisera from that immunized animal. Alternatively, in some embodiments of the present invention, serum is collected from persons who may have been exposed to a particular antigen. Exposure to a particular antigen may occur a work environment, such that those persons have been occupationally exposed to a particular antigen and have developed polyclonal antibodies to a peptide, polypeptide, or protein. In some embodiments of the invention polyclonal serum from occupationally exposed persons is used to identify antigenic regions in the gelonin toxin through the use of immunodetection methods.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As also well known in the art, the immunogenicity of a particular immunogen composition can be enhanced by the use of non-specific stimulators of the immune response, known as adjuvants. Suitable molecule adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection also may be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified polypeptide, peptide or domain, be it a wild-type or mutant composition. The immunizing composition is administered in a manner effective to stimulate antibody producing cells.

mAbs may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate mAbs. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

b. Immunodetection Methods

As discussed, in some embodiments, the present invention concerns immunodetection methods for binding, purifying, removing, determining, and/or otherwise detecting biological components such as antigenic regions on polypeptides and peptides. The immunodetection methods of the present invention can be used to identify antigenic regions of a peptide, polypeptide, or protein that has therapeutic implications, particularly in reducing the immunogenicity or antigenicity of the peptide, polypeptide, or protein in a target subject.

Immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature, such as, e.g., Doolittle et al., 1999; Gulbis et al., 1993; De Jager et al., 1993; and Nakamura et al., 1987, each incorporated herein by reference.

In general, the immunobinding methods include obtaining a sample suspected of containing a protein, polypeptide and/or peptide, and contacting the sample with a first antibody, monoclonal or polyclonal, in accordance with the present invention, as the case may be, under conditions effective to allow the formation of immunocomplexes.

These methods include methods for purifying a protein, polypeptide and/or peptide from organelle, cell, tissue or organism's samples. In these instances, the antibody removes the antigenic protein, polypeptide and/or peptide component from a sample. The antibody will preferably be linked to a solid support, such as in the form of a column matrix, and the sample suspected of containing the protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen or antigenic domain, and contact the sample with an antibody against the antigen or antigenic domain, and then detect and quantify the amount of immune complexes formed under the specific conditions.

In terms of antigen detection, the biological sample analyzed may be any sample that is suspected of containing an antigen or antigenic domain, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

i. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, antibodies are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label. The ELISA may be based on differential binding of an antibody to a protein with Arg389 versus Gly389.

In another exemplary ELISA, the samples suspected of containing the antigen are immobilized onto the well surface and/or then contacted with antibodies. After binding and/or washing to remove non-specifically bound immune complexes, the bound anti-antibodies are detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

ii. Immunohistochemistry

The antibodies of the present invention may also be used in conjunction with both fresh-frozen and/or formalin-fixed, paraffin-embedded tissue blocks prepared for study by immunohistochemistry (IHC). For example, immunohistochemistry may be utilized to characterize Fortilin or to evaluate the amount Fortilin in a cell. The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 mg of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

IV. THERAPY

Once the genotype or the protein sequence of an endothelin gene system member of an individual is determined, a therapeutic course of treatment may be individualized. In one embodiment of the method, the trait of interest is a clinical response exhibited by a patient to some therapeutic treatment, for example, response to a β-adrenergic receptor targeting agent. As used herein the term "clinical response" means any or all of the following: a quantitative measure of the efficacy or potency of the therapy and adverse events (i.e., side effects).

Thus, for example, individuals that are homozygous for an adenosine at nucleotide position +356 in intron 4 of EDN1 (rs2071942) having a medical condition can be placed on a therapy that includes a β-adrenergic receptor targeting agent such as but not limited to bucindolol. The β-adrenergic receptor targeting agent may be administered alone or in combination with at least one other agent, such as a stabilizing compound. The β-adrenergic receptor targeting agent may also be administered in combination with a medical device that would have previously been contraindicated by the disease state that required the device.

A. Routes of Administration

Administration of a β-adrenergic receptor targeting agent may be by any number of routes including, but not limited to oral, intravenous, intramuscular, intra-arterial, intramedullary, intrathecal, intraventricular, intradermal, intratracheal, intravesicle, intraocular, transdermal, subcutaneous, intraperitoneal, intranasal, enteral, topical, sublingual, or rectal. Further details on techniques for formulation and administration may be found in the latest edition of Remington's Pharmaceutical Sciences (Mack Publishing Co., Easton, Pa.). In certain embodiments, a β-adrenergic receptor targeting agent is formulated for oral administration.

B. Formulations

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

1. Controlled/Extended/Sustained/Prolonged Release Administration

Another aspect of this invention provides methods of treating heart failure patients by delivering the β-adrenergic receptor targeting agent to a patient as a controlled release formulation. As used herein, the terms "controlled," "extended," "sustained," or "prolonged" release of the composition of the present invention will collectively be referred to herein as "controlled release," and includes continuous or discontinuous, and linear or non-linear release of the composition of the present invention. There are many advantages for a controlled release formulation of β-adrenergic receptor targeting agents.

a. Tablets

A controlled release tablet suitable for purposes of this invention is disclosed in U.S. Pat. No. 5,126,145, which is incorporated by reference herein. This tablet comprises, in admixture, about 5-30% high viscosity hydroxypropyl methyl cellulose, about 2-15% of a water-soluble pharmaceutical binder, about 2-20% of a hydrophobic component such as a waxy material, e.g., a fatty acid, and about 30-90% active ingredient.

b. Films

This invention further provides a prophylaxis for or method of treating a patient following an invasive cardiac procedure comprising administering biodegradable, biocompatible polymeric film comprising a β-adrenergic receptor targeting agent, such as bucindolol, to a patient. The polymeric films are thin compared to their length and breadth. The films typically have a uniform selected thickness between about 60 micrometers and about 5 mm. Films of between about 600 micrometers and 1 mm and between about 1 mm and about 5 mm thick, as well as films between about 60 micrometers and about 1000 micrometers, and between about 60 and about 300 micrometers are useful in the manufacture of therapeutic implants for insertion into a patient's body. The films can be administered to the patient in a manner similar to methods used in adhesion surgeries. For example, a β-adrenergic receptor targeting agent, such as bucindolol, film formulation can be sprayed or dropped onto a cardiac tissue site or artery during surgery, or a formed film can be placed over the selected tissue site. In an alternative embodiment, the film can be used as controlled release coating on a medical device such as a stent, as is discussed in further detail below.

Either biodegradable or nonbiodegradable polymers may be used to fabricate implants in which the β-adrenergic receptor targeting agent is uniformly distributed throughout the polymer matrix. A number of suitable biodegradable polymers for use in making the biodegradable films of this invention are known to the art, including polyanhydrides and aliphatic polyesters, preferably polylactic acid (PLA), polyglycolic acid (PGA) and mixtures and copolymers thereof, more preferably 50:50 copolymers of PLA:PGA and most preferably 75:25 copolymers of PLA:PGA. Single enantiomers of PLA may also be used, preferably L-PLA, either alone or in combination with PGA. Polycarbonates, polyfumarates and caprolactones may also be used to make the implants of this invention.

The amount of the β-adrenergic receptor targeting agent, such as bucindolol, to be incorporated into the polymeric films of this invention is an amount effective to show a measurable effect in treating diseases having similar pathophysiological states, such as but not limited to, heart failure, cardiac arrhythmias, hypertension and cardiomyopathy. The composition of the present invention can be incorporated into the film by various techniques such as by solution methods, suspension methods, or melt pressing.

c. Transdermal Patch Device

Transdermal delivery involves delivery of a therapeutic agent through the skin for distribution within the body by circulation of the blood. Transdermal delivery can be compared to continuous, controlled intravenous delivery of a drug using the skin as a port of entry instead of an intravenous needle. The therapeutic agent passes through the outer layers of the skin, diffuses into the capillaries or tiny blood vessels in the skin and then is transported into the main circulatory system.

Transdermal patch devices which provide a controlled, continuous administration of a therapeutic agent through the skin are well known in the art. Such devices, for example, are disclosed in U.S. Pat. Nos. 4,627,429; 4,784,857; 5,662,925; 5,788,983; and 6,113,940, which are all incorporated herein by reference. Characteristically, these devices contain a drug impermeable backing layer which defines the outer surface of the device and a permeable skin attaching membrane, such as an adhesive layer, sealed to the barrier layer in such a way as to create a reservoir between them in which the therapeutic agent is placed. In one embodiment of the present invention a formulation of the β-adrenergic receptor targeting agent is introduced into the reservoir of a transdermal patch and used by a patient who is homozygous for an adenosine at nucleotide position +356 in intron 4 of EDN1 (rs2071942).

d. Medical Devices

Another embodiment contemplates the incorporation of a β-adrenergic receptor targeting agent, such as bucindolol, into a medical device that is then positioned to a desired target location within the body, whereupon the β-adrenergic receptor targeting agentelutes from the medical device. As used herein, "medical device" refers to a device that is introduced temporarily or permanently into a mammal for the prophylaxis or therapy of a medical condition. These devices include any that are introduced subcutaneously, percutaneously or surgically to rest within an organ, tissue or lumen. Medical devices include, but are not limited to, stents, synthetic grafts, artificial heart valves, artificial hearts and fixtures to connect the prosthetic organ to the vascular circulation, venous valves, abdominal aortic aneurysm (AAA) grafts, inferior venal caval filters, catheters including permanent drug infusion catheters, embolic coils, embolic materials used in vascular embolization (e.g., PVA foams), mesh repair materials, a Dracon vascular particle orthopedic metallic plates, rods and screws and vascular sutures.

In one embodiment, the medical device such as a stent or graft is coated with a matrix. The matrix used to coat the stent or graft according to this invention may be prepared from a variety of materials. A primary requirement for the matrix is that it be sufficiently elastic and flexible to remain unruptured on the exposed surfaces of the stent or synthetic graft.

C. Dosages

The amount of a β-adrenergic receptor targeting agent that is administered or prescribed to the patient can be about, at least about, or at most about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg, or any range derivable therein. Alternatively, the amount administered or prescribed may be about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mg/kg, or any range derivable therein, with respect to the weight of the patient.

When provided in a discrete amount, each intake of a β-adrenergic receptor targeting agent can be considered a "dose." A medical practitioner may prescribe or administer multiple doses of bucindolol over a particular time course (treatment regimen) or indefinitely.

A β-adrenergic receptor targeting agent may be administered 1, 2, 3, 4, 5, 6, 7, 8, 9, 10, 11, 12, 13, 14, 15, 16, 17, 18, 19, 20, 30, 40, 50, 60, 70, 80, or more times or any range derivable therein. It is further contemplated that the drug may be taken for an indefinite period of time or for as long as the patient exhibits symptoms of the medical condition for which a β-adrenergic receptor targeting agent was prescribed or administered. Also, the drug may be administered every 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more, or any range derivable therein. Alternatively, it may be administered systemically over any such period of time and be extended beyond more than a year.

D. Other Therapeutic Options

In another embodiment, it is envisioned to use a β-adrenergic receptor targeting agent in combination with other therapeutic modalities. Thus, in addition to the therapies described above, one may also provide to the patient more "standard" pharmaceutical cardiac therapies. Examples of other therapies include, without limitation, other beta blockers, anti-hypertensives, cardiotonics, anti-thrombotics, vasodilators, hormone antagonists, inotropes, diuretics, endothelin antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using a β-adrenergic receptor targeting agent may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either β-adrenergic receptor targeting agent or the other agent will be desired. In this regard, various combinations may be employed. By way of illustration, where the β-adrenergic receptor targeting agent is "A" and the other agent is "B", the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are likewise contemplated.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Endothelin Gene System Member Analysis—Methodology

Clinical Studies.

309 subjects with idiopathic dilated cardiomyopathy were studied from the Beta-Blocker Evaluation of Survival Trial (BEST) (2001). BEST was a multicenter, randomized, prospective trial of patients with NYHA class III or IV heart failure and an ejection fraction <35% comparing mortality in adults treated with placebo or the non-selective β-blocker bucindolol. The BEST DNA bank, initiated in the study's second year, collected samples from 38% of the original participants. The inventors requested samples from idiopathic dilated cases, rather than the entire cohort, to ensure a more homogenous heart failure population. In particular, the inventors sought to avoid studying genetic ischemic forms of heart failure where acquired macrovascular changes in arterial stiffness or tone could potentially mask or override inherent microvascular phenotypes mediated by variation in endothelin genes. Written informed consent was obtained from each participant and all DNA was coded to maintain confidentiality. The genotyping project was approved by the BEST DNA Bank Oversight Committee and by the Colorado Multiple Institutional Review Board Selection of EGS Polymorphisms.

EGS SNPs were selected prior to the release of HapMap data using an extensive literature review and a search of the NCBI SNP database (dbSNP build 108). The six EGS genes studied included three endothelin genes (EDN1, EDN2, EDN3), both endothelin receptors A and B (EDNRA, EDNRB) and the endothelin converting enzyme 1 (ECE1). SNPs predicting changes in amino acid sequence of EGS proteins were prioritized for study. SNPs in non-coding regions (intronic and promoter regions) and synonymous SNPs were also studied when prior reports suggested a positive association with a phenotype in humans and/or a functional effect had been demonstrated in an in vitro model. Twenty-two EGS SNPs, including fifteen nonsynonymous SNPs, were identified by searching published literature and the dbSNP database (Table 1) (Herrmann et al., 2001; Charron et al., 1999; Vasku et al., 2002). At the start of the study, population frequencies of thirteen EGS SNPs were not reported in dbSNP and these SNPs proved rare in the population and were not analyzed further (rs#: 5798, 5799, 457755, 457651, 5345, 5346, 1801710, 2228271, 5347, 5350, 5352, 3026902, 3026906). Nine SNPs in four genes with minor allele frequencies of 5% or greater and were included in the statistical analysis. In silico analyses of EGS SNPs for predicted effects on protein secondary structure used GOR IV and PSIPRED algorithms (Garnier et al., 1996; Jones, 1999); possible effects on splicing used in the GeneSplicer program (Pertea et al., 2001).

TABLE 1

Endothelin Gene System Polymorphisms Initially Selected for Study

| Gene | rs number | SNP | Protein | Location | NCBI MAF | BEST MAF (n = 309) |
|---|---|---|---|---|---|---|
| EDN1 | 1800997 | −138 DelA | No change | 5' UTR | 0.19 | 0.25 |
|  | 5369 | G/A | Glu106 | Exon 3 | 0.11 | 0.12 |
|  | 2071942 | G/A | No change | IVS-4 | 0.16 | 0.25 |
|  | 5370 | G/T | Lys198Asn | Exon 5 | 0.26 | 0.24 |
| EDNRA | 1801708 | A/G | No change | 5' UTR | 0.49 | 0.44 |
|  | 5333 | C/T | His323 | Exon 6 | 0.31 | 0.34 |
|  | 5343 | C/T | No change | 3' UTR | 0.25 | 0.34 |
| EDNRB | 5351 | A/G | Leu277 | Exon 5 | 0.43 | 0.41 |
| ECE1 | 1076669 | C/T | Thr341Ile | Exon 9 | 0.04 | 0.07 |

SNP—single nucleotide polymorphism;
UTR—untranslated region;
IVS—intervening sequence (intron);
allele frequency for rs1800997 [Charron et al., 1999];
MAF—Minor allele frequency listed as reported in NCBI dbSNP (build 127).
BEST—Beta Blocker Evaluation of Survival Trial;
NR = not reported Genotyping.

Genotyping was performed by the University of Colorado Cardiovascular Institute laboratory using a MSQ96 MA Pyrosequencer (Biotage, Uppsala, Sweden) and primers were designed using software provided by the manufacturer. PCR reactions were first performed with primer pairs flanking each SNP; one of each primer pair also contained an M13 sequence (5',5'-Biotin-CAGGAAACAGCTATGAC-3') (SEQ ID NO:1) to allow for incorporation of a biotinylated 'universal' primer containing the same M13 sequence. Pyrosequencing was then performed using sequencing primers designed specifically for each SNP.

For rs5370, the assay used the following primers: forward-CTTCTTTTGCCAAAGGGTGA (SEQ ID NO:2), reverse-biotin-AGGGTGGAGAGTGCAGAGTC (SEQ ID NO:3), sequencing-CCAAGCTGAAAGGCA (SEQ ID NO:4). For rs2071942 the assay used the following primers: forward-biotin-CAGGAAACAGCTATGACCAGCCTTT-GCCTCTCTGAGTC (SEQ ID NO:5), reverse-GGC-CATCTGAATAACTGCAAC (SEQ ID NO:6) sequencing-GCTCCCCAAAATGAT (SEQ ID NO:7). Results for selected SNPs underwent repeat genotyping of a random subset of 10% of the samples for validation and quality control.

Statistical Analysis.

Time to each of two endpoints was examined: all cause death and a combined endpoint comprised of first heart failure hospitalization or all cause death, using the Cox proportional hazards model. Genotype was treated a priori as a continuous variable, consistent with an allele dosage effect. Analyses were conducted using R and SAS. Primary analyses consisted of separate tests of a main genotype effect on time to event for each SNP within each treatment arm: placebo (N=159) and bucindolol (N=150). Secondary analyses, in the combined sample (N=309), consisted of tests of a genotype-treatment pharmacogenetic interaction and of a main genotype effect independent of treatment arm. Secondary analyses, comprised of interaction tests and estimation of within-genotype bucindolol:placebo hazard ratios, were also performed. Ethnicity was not included as a factor in initial Cox models, because of the relatively small sample. However, post-hoc analyses (within ethnic group, and including ethnicity-genotype interactions) were used to explore whether initial results were due to unaccounted for ethnic stratification. Linkage disequilibrium was assessed by taking the $R^2$ value (squared correlation) of the genotypes (coded as 0, 1 or 2) between two SNPs.

The inventors had two a priori reasons for emphasizing within-treatment arm effects, over the more usual interaction test. As a gene-treatment interaction effect cannot exist without a main genetic effect in at least one of the treatment groups, the first test investigated whether there was any such main genetic effect before testing whether that effect differed in a way that depended on treatment (i.e., a pharmacogenetic interaction). Second, relative power with approximately equal sample sizes was examined, assuming a possible pharmacogenetic effect with no or a negligible effect of genotype in one group, say the placebo group, and a more substantial effect in the other, active-drug, group. In that case, the values of the active-drug genotype effect and the interaction effect (written as the difference of within-treatment effects) are the same. The standard error of the interaction effect is approximately $\sqrt{2} \times S$, where S is the standard error of the within-treatment effect. Thus, the most powerful test for any type of genotype effect in this setting is the within-treatment test in the arm with a genetic effect. This is generally true, unless the genetic effects work in opposite directions in the two treatment arms. The test for a main genotype effect, independent of treatment group, would be the most powerful in the absence of a pharmacogenetic effect.

To account for the large number of simultaneous tests, adjusted p-values obtained from a multiple-testing permutation procedure are reported (Westfall and Young, 1993). Based on the actual data set, 5000 random data sets were generated by randomly permuting the time to event data relative to the genotype data, separately for patients on placebo and for patients on bucindolol. Adjusted p-values for all within treatment arm tests are based on 36 comparable tests (2 outcomes×2 treatment arms×9 SNPs). Adjusted p-values for interaction tests are based on 18 tests (2 outcomes×9 SNPs).

Cox model analysis was also used to examine a variety of more complicated models, and to describe the quantify the effects of bucindolol in terms of bucindolol:placebo hazard ratios, within genotype. Kaplan-Meier plots and log-rank tests were also examined. All p-values were based on two-sided tests. The statistical analysis was performed at the Veterans Affairs Cooperative Studies Program DNA Bank Coordinating Center.

Example 2

Demographic and Clinical Characteristics of Test Groups

The placebo and bucindolol groups were similar with respect to demographic and clinical characteristics (Table 2). There were no significant differences between the placebo and bucindolol groups with respect to baseline heart rate, systolic blood pressure, body mass index, or baseline cardiovascular medications. Genotype frequencies at all nine EGS SNPs were consistent with prior reports (Table 1). All but one SNP were in Hardy-Weinberg equilibrium; disequilibrium at EDNRA A/G (5'UTR) appeared to be generated by ethnic stratification, since genotypes were in Hardy-Weinberg equilibrium when analyzed within each ethnic group.

TABLE 2

| | Comparison of treatment groups | | |
|---|---|---|---|
| Variable | Placebo (N = 159) | Bucindolol (N = 150) | p-value* |
| Median Age (years) | 57.0 | 59.0 | 0.50 |
| Gender | | | |
| Male | 106 (67%) | 107 (71%) | 0.38 |
| Female | 53 (33%) | 43 (29%) | |
| Race | | | |
| NonBlack | 128 (81%) | 112 (75%) | 0.22 |
| Black, non-Hispanic | 31 (19%) | 38 (25%) | |
| NHYA Class | | | |
| Class III | 151 (95%) | 141 (94%) | 0.71 |
| Class IV | 8 (5%) | 9 (6%) | |
| Median duration of HF (months) | 24.0 | 26.5 | 0.94 |
| Diabetes | 39 (25%) | 50 (33%) | 0.09 |
| Hypertension | 72 (45%) | 76 (51%) | 0.34 |
| Current Tobacco Use | 23 (14%) | 20 (13%) | 0.77 |
| Mean Arterial Pressure (SD) | 87.4 (11.8) | 88.2 (12.3) | 0.56 |
| Mean LVEF (SD) | 24.5 (7.0) | 24.5 (7.0) | 0.93 |
| Mean Serum creatinine mg/dL (SD) | 1.1 (0.3) | 1.2 (0.3) | 0.08 |

TABLE 2-continued

| | Comparison of treatment groups | | |
|---|---|---|---|
| Variable | Placebo (N = 159) | Bucindolol (N = 150) | p-value* |
| Mean Plasma Norepinephrine pg/ml (SD) | 460.5 (311) | 468.3 (253) | 0.83 |

Example 3

Identification of Two SNPs with Beneficial Treatment Effects

After controlling for multiple testing, no EGS variant had a significant effect on time to all cause death in either treatment arm, or on time to the combined outcome in patients on placebo. However, two SNPs in EDN1 (G/T Lys198Asn and G/A (IVS-4)) had highly significant genotype effects on time to the combined endpoint of first heart failure hospitalization or all cause death for patients on bucindolol, even after rigorous adjustment for multiple tests (FIG. 1, Table 3). The alleles in the more common G-Lys haplotype were each associated with a better outcome. This pharmacogenetic interaction resulted in an apparent beneficial effect of bucindolol in the common homozygotes, a harmful effect in the rare homozygotes and a neutral effect in the heterozygotes (Table 4). Only the beneficial effect in the common homozygote group, which had the largest numbers of subjects and events, was statistically significant. Hospitalization was not considered a primary or secondary endpoint in BEST and is not included in the reported analyses. Results for hospitalization are similar to those for the combined endpoint. However, the inventors felt including another post hoc analysis would not add to the results. When hospitalization alone is considered, excluding deaths without prior hospitalization appears to decrease precision, increasing the standard error by about 10%.

G/A (IVS-4) and Lys198Asn were in tight linkage disequilibrium (genotype $R^2$=0.85), appearing primarily in unphased genotypes consistent with the G-Lys and A-Asn haplotypes. Thus, it was not possible to distinguish statistically between the SNPs relative importance in a two-SNP model. Neither SNP was independently statistically significant in the presence of the other, although the null model with neither SNP was clearly rejected. EDN1 G/A (IVS-4) and Lys198Asn also had significant treatment-genotype interactions (Table 3).

Two other SNPs, EDN1 Glu106 (p=0.04) and ECE1 Thr341Ile (p=0.03) had significant main effects for the combined outcome, but were not significant after adjustment for multiple tests. EDNRA His323 (p=0.03) had a significant treatment-genotype interaction for time to all-cause death, before adjustment for multiple tests. The test for a main genotype effect in the combined data set yielded no significant results for either outcome.

TABLE 3

| Effects of One-Allele Changes in the Allele Dosage Cox Model | | | | | | | | | |
|---|---|---|---|---|---|---|---|---|---|
| Treatment | SNP | Group | N | E | MAF | HR | 95% CI | p | adj p* |
| Bucindolol | G/A (IVS-4) | All | 150 | 49 | 25% | 2.2 | 1.4-3.3 | <0.001 | 0.01 |
| | | Non-Hispanic Whites | 100 | 27 | 24% | 1.9 | 1.09-3.45 | 0.02 | |
| | | Non-Hispanic Blacks | 38 | 16 | 22% | 1.58 | 0.67-3.76 | 0.30 | |
| | Lys198Asn | All | 150 | 49 | 24% | 2.0 | 1.3-3.0 | 0.001 | 0.03 |
| | | Non-Hispanic Whites | 100 | 27 | 23% | 1.9 | 1.05-3.30 | 0.03 | |
| | | Non-Hispanic Blacks | 38 | 16 | 22% | 1.5 | 0.75-3.10 | 0.25 | |

TABLE 3-continued

Effects of One-Allele Changes in the Allele Dosage Cox Model

| Treatment | SNP | Group | N | E | MAF | HR | 95% CI | p | adj p* |
|---|---|---|---|---|---|---|---|---|---|
| Placebo | G/A (IVS-4) | All | 159 | 61 | 25% | 0.83 | 0.5-1.3 | 0.41 | 1.00 |
| | | Non-Hispanic Whites | 112 | 41 | 25% | 0.9 | 0.55-1.60 | 0.8 | |
| | | Non-Hispanic Blacks | 31 | 16 | 26% | 0.5 | 0.21-1.20 | 0.12 | |
| | Lys198Asn | All | 158 | 60 | 25% | 0.9 | 0.6-1.3 | 0.48 | 1.00 |
| | | Non-Hispanic Whites | 111 | 40 | 24% | 0.9 | 0.54-1.60 | 0.78 | |
| | | Non-Hispanic Blacks | 31 | 16 | 27% | 0.5 | 0.22-1.21 | 0.13 | |

Data shown are for combined endpoint (first heart failure hospitalization or all-cause mortality); HR-hazard ratios associated wish each copy of allele A or Asn, respectively, under an allele dosage model. For bucindolol by SNP interaction tests, p values (adjusted p values**) were 0.002 (0.03) and 0.006 (0.07) for IVS-4 and Lys198Asn, respectively. A non-significant trend for interaction was observed for both SNPs for both ethnic subgroups.
*adjusted p value for 36 tests of genotype within treatment arm in primary analysis.
**Adjusted p values for 18 interaction tests.
Post-hoc analyses by ethnic sub-group were not inducted in p value adjustments.
N—number of subjects (All includes subjects from other ethnicities);
E—number of events;
MAF—minor allele frequency in sample

TABLE 4

Hazard Ratios for Bucindolol Versus Placebo by EDN1 Genotype

| SNP | Group | N* | E | HR | 95% CI | p value |
|---|---|---|---|---|---|---|
| G/A (IVS-4) | GG | 171 | 56 | 0.5 | 0.3-0.9 | 0.01 |
| | GA | 121 | 44 | 1.1 | 0.6-1.9 | 0.85 |
| | AA | 17 | 10 | 3.2 | 0.8-12.5 | 0.10 |
| Lys198Asn | Lys/Lys | 176 | 58 | 0.5 | 0.3-0.9 | 0.02 |
| | Lys/Asn | 115 | 41 | 1.1 | 0.6-2.0 | 0.77 |
| | Asn/Asn | 17 | 10 | 2.5 | 0.6-9.9 | 0.19 |

Data shown are for combined endpoint (first heart failure hospitalization or all cause mortality);
N—number of subjects;
E—number of events;
HR—hazard ratio;
95% CI—95% confidence interval;
*One individual was not successfully genotyped at Lys198Asn Example 4

Secondary Analyses: Ethnic Study

Since Blacks were previously reported to experience a worse response in BEST, the inventors conducted secondary analyses in the two largest ethnic subgroups: non-Hispanic Blacks and non-Hispanic Whites. Both G/A (IVS-4) and Lys198Asn showed significant effects for the combined outcome in non-Hispanic Whites in the bucindolol treated group; in Blacks where the sample size was much smaller, the hazard ratios were consistent, but no longer significant. In each group, there was a non-significant trend for a treatment-SNP interaction for both G/A (IVS-4) and Lys198Asn. ECE1 Thr341Ile could not be tested in non-Hispanic Blacks, which included a single carrier of the minor allele. Its signficance in bucindolol treated subjects increased when the analysis was restricted to non-Hispanic Whites (p=0.008). EDN1 Glu106 was significant in non-Hispanic Whites (p=0.03), but not in non-Hispanic Blacks.

Example 5

Two-SNP Models Including Either EDN1 G/A (IVS-4) or Lys198Asn

All possible two-SNP models were tested, including either EDN1 G/A (IVS-4) or Lys198Asn and one of the remaining seven SNPs, both with and without a SNP-SNP interaction term, in post-hoc analyses. ECE1 Thr341Ile was significant in the two-SNP models including either EDN1 G/A (IVS-4) (p=0.04) or Lys198Asn (p=0.04), but only in the no-interaction models. Thus, ECE1 Thr341Ile might contribute an effect on the combined outcome independent of the EDN1 SNPs. In the EDN1 Lys198Asn-ECE1 Thr341Ile model, the hazard ratios (HRs) are 1.97 (95% CI 1.31, 2.96) and 1.81 (95% CI 1.04, 3.15), respectively. In the EDN1 G/A (IVS-4)-ECE1 Thr341Ile model, the HRs are 2.09 (95% CI 1.37, 3.20) and 1.78 (95% CI 1.02, 3.12), respectively. Thus, the effect of the ECE1 SNP is estimated to be almost as strong as those of the two EDN1 variants. The weaker statistical significance for ECE1 Thr341Ile may be due to its less balanced allele frequencies, which reduce power. In contrast, EDN1 Glu106 was no longer significant when added to a model including either G/A (IVS-4) or Lys198Asn. Thus, the significance of EDN1 Glu106 in a one-SNP model might merely reflect its highly significant linkage disequilibrium with those SNPs (p<0.001).

Results were qualitatively unchanged in other post hoc analyses. Liggett et al. (2006) previously genotyped reduced all-cause mortality in bucindolol treated subjects carrying the Arg-389 allele of the beta-1-adrenergic receptor (ADRB) in the 1040 BEST DNA Bank subjects. This sample represents a subset of that earlier study. The inventors obtained these genotypes for the subjects and fit two-SNP models with one EDNS SNP and the ADRB Gly389Arg variant as described in the previous paragraph. The inventor's estimates and significance results were qualitatively unchanged.

For all SNPs that were significant under the allele-dosage model used in primary analyses, neither a dominant nor a recessive genetic model fit better based on the value of the log-likelihood. In some of these cases, either the dominant or recessive model failed to detect significance. No non-significant SNP in the primary analyses became significant under a recessive of dominant model. Post hoc adjustment for possibly confounding effects of medications did not qualitatively affect primary SNP results. A secondary logistic regression analysis of genetic effects on adverse events found no significant results, when adjusted for multiple tests.

The foregoing description is considered as illustrative only of the principles of the invention. Further, since numerous modifications and changes will readily occur to those skilled in the art, it is not desired to limit the invention to the exact construction and process as described above. Accordingly, all suitable modifications and equivalents may be resorted to falling within the scope of the invention as defined by the claims that follow.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,582,788
U.S. Pat. No. 4,627,429
U.S. Pat. No. 4,659,774
U.S. Pat. No. 4,683,194
U.S. Pat. No. 4,683,195
U.S. Pat. No. 4,683,202
U.S. Pat. No. 4,784,857
U.S. Pat. No. 4,800,159
U.S. Pat. No. 4,816,571
U.S. Pat. No. 4,883,750
U.S. Pat. No. 4,946,773
U.S. Pat. No. 4,959,463
U.S. Pat. No. 4,965,188
U.S. Pat. No. 5,126,145
U.S. Pat. No. 5,130,238
U.S. Pat. No. 5,141,813
U.S. Pat. No. 5,169,766
U.S. Pat. No. 5,264,566
U.S. Pat. No. 5,279,721
U.S. Pat. No. 5,428,148
U.S. Pat. No. 5,554,744
U.S. Pat. No. 5,574,146
U.S. Pat. No. 5,602,244
U.S. Pat. No. 5,605,798
U.S. Pat. No. 5,645,897
U.S. Pat. No. 5,662,925
U.S. Pat. No. 5,705,629
U.S. Pat. No. 5,788,983
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,952,174
U.S. Pat. No. 6,066,502
U.S. Pat. No. 6,113,940
U.S. Pat. No. 4,656,127
U.S. Pat. No. 4,682,195
U.S. Pat. Ser. No. 2003/0176412

Abbondanzo et al., *Breast Cancer Res. Treat.*, 16:182(151), 1990.
Allred et al., *Arch. Surg.*, 125(1):107-113, 1990.
Arinami et al., *Am. J. Hum. Genet.*, 48:990-996, 1991.
Ausubel et al., In: *Current Protocols in Molecular Biology*, John, Wiley & Sons, Inc., New York, 1989.
Barany, et al., *Proc. Natl. Acad. Sci. USA*, 88:189-193, 1991.
Barden et al., *J. Hypertens.*, 19:1775-82, 2001.
Bellus, *J. Macromol. Sci. Pure Appl. Chem.*, A31(1): 1355-1376, 1994.
Beta-Blocker Evaluation of Survival Trial Investigators, *N. Engl. J. Med.*, 344:1659-67, 2001.
Bianchetti et al., *Br. J. Pharmacol.*, 100:831-839, 1990.
Bond et al., *Br. J. Pharmacol.*, 95:723-734, 1988.
Bristow et al., *Circ. Res.*, 59(3):297-309, 1986.
Bristow et al., *Mol. Pharmacol.*, 35:296-303, 1988.
Brodde et al., *J. Cardiovasc., Pharmacol.*, 8:1235-1242, 1986.
Brodde et al., *Z. Kardiol.*, 81:71-78, 1992.
Brown et al., *Immunol Ser*, 53:69-82, 1990.
Brugada et al., *J Investig. Med.*, 45:542-51, 1997.
Capaldi et al., *Biochem. Biophys. Res. Comm.*, 74(2):425-433, 1977.
Charron et al., *Eur. Heart J.*, 20:1587-91, 1999. CIBIS-II Investigators, *Lancet*, 353:9-13, 1999.
Coleman et al., *Brit. J. Pharmacology Proc. Supl.*, 90:40, 1987.
de Arruda et al., *Expert Rev. Mol. Diagn.*, 2(5):487-496, 2002.
De Jager et al., *Semin. Nucl. Med.*, 23(2):165-179, 1993.

Diefenbach et al., *Genet. Test.*, 10:163-8, 2006.
Dohlman et al., *Annu. Rev. Biochem.*, 60:653-688, 1991.
Doolittle et al., *Methods Mol. Biol.*, 109:215-237, 1999.
Dzau, *Curr. Opin. Nephrol. Hypertens.*, 2:27-32, 1993.
Effect of metoprolol CR/XL in chronic heart failure: Metoprolol CR/XL Randomised Intervention Trial in Congestive Heart Failure (MERIT-HF), *Lancet*, 353:2001-7, 1999.
Emorine et al., *Science*, 245:1118-1121, 1989.
Emoto and Yanagisawa, *J. Biol. Chem.*, 270:15262-15268, 1995.
European Appln. 201,184
European Appln. 237,362
European Appln. 258,017
European Appln. 266,032
European Appln. 320,308
European Appln. 329,822
European Appln. 50,424
European Appln. 84,796
Evans et al., *Nature*, 429:464-8, 2004.
French Appln. 2,650,840
Frielle et al., *Proc. Natl. Acad. Sci. USA*, 84:7920-7924, 1987.
Froehler et al., *Nucleic Acids Res.*, 14(13):5399-5407, 1986.
Frohman, In: *PCR Protocols: A Guide To Methods And Applications*, Academic Press, N.Y., 1990.
Gamier et al., *Methods Enzym.*, 266:540-53, 1996.
Giannessi et al., *Pharmacol. Res.*, 43:111-26, 2001.
Granneman et al., *J. Pharmacol. Exp. Ther.*, 256:421-425, 1991.
Great Britain Appln 2 202 328
Gulbis and Galand, *Hum. Pathol.*, 24(12):1271-1285, 1993.
Halushka et al., *Nat. Genet.*, 22(3):239-247, 1999.
Harlow and Lane, In: *Antibodies: A Laboratory Manual*, Cold Spring Harbor Laboratory, 1988.
Herrmann et al., *Eur. Heart. J.*, 22:1948-53, 2001.
Hiroe et al., *Am. J. Cardiol.*, 68:1114-5, 1991.
Hjalmarson et al., *J. Am. Med. Assoc.*, 283:1295-1302, 2000.
Humphries et al., In: *Molecular Diagnosis of Genetic Diseases*, Elles (Ed.), 321-340, 1996.
Iemitsu et al., *Hypertension*, 47:928-936, 2006.
Iglarz et al., *Hypertension*, 39:209-13, 2002.
Ikeda et al., *Biochem. Biophys. Res. Commun.*, 293:421-426, 2002.
Inazuka et al., *Genome Res*, 7(11):1094-1103, 1997.
Innis et al., *Proc. Natl. Acad. Sci. USA*, 85(24):9436-9440, 1988.
Inoue et al., *Proc. Natl. Acad. Sci. USA*, 86:2863-2867, 1989.
Jin et al., *Hypertension*, 41:163-7, 2003.
Johnson et al., *Nat. Genet.*, 29(2):233-237, 2001.
Jones, *Nature*, 199:280-282, 1963.
Jones, *J. Mol. Biol.*, 292:195-202, 1999.
Kaandorp et al., *Heart*, 91:1471-1472, 2005.
Ke and Cardon *Bioinformatics*, 19(2):287-288, 2003.
King et al., *Genome Res.*, 15:1051-60, 2005.
Ko et al., *Endocrin.*, 147:1770-1779, 2006.
Kobilka et al., *Proc. Natl. Acad. Sci. USA*, 84:46-50, 1987.
Kolbe et al., *Genome Res.*, 14:700-7, 2004.
Komher, et al., *Nucl. Acids. Res.* 17:7779-7784, 1989.
Kozak et al., *J. Cardiovasc. Pharmacol.*, 44:S92-S95, 2004.
Krum et al., *Am. Heart J.*, 131:337-41, 1996.
Kuppuswamy et al., *Proc. Natl. Acad. Sci. USA*, 88:1143-1147, 1991.
Kwoh et al., *Proc. Natl. Acad. Sci. USA*, 86:1173, 1989.
Kwok et al., *Genomics*, 31(1):123-6, 1996.
Kwok and Chen, *Curr. Issues Mol. Biol.*, April; 5(2):43-60, 2003.
Kwok et al., *Genomics*, 23(1):138-144, 1994.
Kwok, *Annu. Rev. Genomics Hum. Genet.*, 2:235-258, 2001.
Landegren et al., *Science* 241:1077-1080, 1988.
Leizorovicz et al., *Am. Heart J.*, 143(2):301-307, 2002.
Levin, *N Engl. J. Med.*, 333:356-63, 1995.
Liggett et al., In: *Catecholamines*, Bouloux (Ed.), W. B. Sounders, London, 1993.
Liggett et al., *Proc. Natl. Acad. Sci. USA*, 103:11288-93, 2006.
Lu et al., *Biopolymers*, 73:606-613, 2004.
Mann et al., *Circulation*, 111(21):2837-2849, 2005.
Maxam et al., *Proc. Natl. Acad. Sci. USA*, 74:560, 1977.
McMurray et al., *Circulation*, 85:1374-9, 1992.
Meiden et al., *J. Biol. Chem.*, 280:40867-40874, 2005.
Meyers et al., *Science*, 230:1242, 1985.
Miyauchi et al., *Annu. Rev. Physiol.*, 61:391-415, 1999.
Modrich, *Ann. Rev. Genet.*, 25:229-253, 1991.
Mosby's Medical, Nursing, & Allied Health Dictionary, (5th Ed.), Mosby, St. Louis, Mo., 1998.
Mullis et al., *Cold Spring Harbor Symp. Quant. Biol.* 51:263-273, 1986.
Nahmias et al., *J. EMBO*, 16(12):3721-3727, 1991.
Nakamura et al., In: *Handbook of Experimental Immunology* (4$^{th}$ Ed.), Weir et al., (eds). 1:27, Blackwell Scientific Publ., Oxford, 1987.
Nambi et al., *Heart Fail. Rev.*, 6:335-40, 2001.
Nicaud et al., *Am. J. Hypertens.*, 12:304-10, 1999.
Nickerson et al., *Proc. Natl. Acad. Sci. USA*, 87:8923-8927, 1990.
Nyren et al., *Anal. Biochem.* 208:171-175, 1993.
Ohara et al., *Proc. Natl. Acad. Sci. USA*, 86:5673-5677, 1989.
Orita et al., *Genomics*, 5:874-879, 1989.
Packer et al., *Circulation*, 106(17):2194-2199, 2002.
Packer et al., *N Engl. J. Med.*, 334:1349-55, 1996.
Packer et al., *N Engl. J. Med.*, 344:1651-1658, 2001.
Pertea et al., *Nucleic Acids Res.*, 29:1185-90, 2001.
PCT Appln. PCT/US87/00880
PCT Appln. PCT/US89/01025
PCT Appln. WO 88/10315
PCT Appln. WO 89/06700
PCT Appln. WO 90/01069
PCT Appln. WO 91/02087
PCT Appln. WO 92/15712
PCT Appln. WO 93/22456
PCT Appln. WO 95/11995
Prezant et al., *Hum. Mutat.*, 1:159-164, 1992.
Remington's Pharmaceutical Sciences, 15th Edition, pages 1035-1038 and 1570-1580.
Ruano et al., *Nucl. Acids Res.*, 19:6877-6882, 1991.
Ruano et al., *Nucl. Acids Res.*, 17:8392, 1989.
Sambrook et al., In: *Molecular cloning*, Cold Spring Harbor Laboratory Press, Cold Spring Harbor, N.Y., 2001.
Sanger et al., *J. Molec. Biol.*, 94:441, 1975.
Sheffield et al., *Proc. Natl. Acad. Sci. USA*, 86:232-236, 1989.
Small et al., *N. Engl. J. Med.*, 347:1135-1142, 2002.
Sokolov, *Nucl. Acids Res.* 18:3671, 1990.
Spieker and Luscher, *Med. Clin. North Am.*, 87:459-74, 2003.
Spieker et al., *J. Am. Coll. Cardiol.*, 37:1493-505, 2001.
Stedman's Medical Dictionary, (25th Ed.), Williams & Wilkins, Baltimore, Md., 1990.
Stevens and Brown, *J. Cardiovasc. Pharmacol.*, 26 Suppl 3:S9-12, 1995.

Stevens et al., *Biotechniques*, 34:198-203, 2003.
Syvanen et al., *Genomics* 8:684-692, 1990.
Taillon-Miller et al., *Genome Res*, 8(7):748-754, 1998.
Tanaka et al., *Hypertens. Res.*, 27:367-71, 2004.
Tiret et al., *Hypertension*, 33:1169-74, 1999.
Turki et al., *J. Clin. Invest.*, 95:1635-1641, 1995.
Turner et al., *Bioessays*, 23:261-269, 2001.
Ugozzoll et al., *GATA* 9:107-112, 1992.
Valdenaire et al., *Eur. J. Biochem.*, 264:341-349, 1999.
Vasku et al., *Exp. Mol. Pathol.*, 73:230-3, 2002.
Walker et al., *Proc. Natl. Acad. Sci. USA*, 89:392-396, 1992.
Wartell et al., *Nucl. Acids Res.*, 18:2699-2706, 1990.
Wei et al., *Circulation*, 89:1580-6, 1994.
Weinshilboum, *N. Engl. J. Med.*, 348:529-37, 2003.
Westfall and Young, In: *Resampling-based multiple testing*, NY Wiley, 46-55, 1993.
Wilkinson, *N Engl. J. Med.*, 352:2211-21, 2005.
Winter et al., *Proc. Natl. Acad. Sci. USA*, 82:7575, 1985.
Yale University School of Medicine Heart Book, Chapter 23, Cardiovascular Drugs (world wide web at .info.med.yale.edu/library/heartbk, Apr. 16, 1999).
Yanagisawa et al., *Nature*, 332:411-5, 1988.
Yang-Feng et al., *Proc. Natl. Acad. Sci. USA*, 87:1516-1520, 1990.
Zhang et al., *J. Cutan. Med. Surg.*, 10:269-276, 2006.

---

The invention claimed is:

1. A method for treating a human patient with a heart condition comprising administering to the patient 5-100 mg of a β-adrenergic receptor targeting agent, after the patient has been determined to have detectable EDN1 protein with an asparagine at amino acid 198 of EDN1 protein and has been genotyped as homozygous for an adenosine at nucleotide position +356 in intron 4 of EDN 1 (r52071942).

2. The method of claim 1, wherein the β-adrenergic receptor targeting agent is a selective or a non-selective β-blocker.

3. A method for treating a patient with a heart condition comprising administering to the patient 5-100 mg of a β-adrenergic receptor targeting agent after the patient has been determined to be homozygous for an adenosine at nucleotide position +346 in intron 4 of EDN1 (rs2071942).

4. The method of claim 3, wherein the β-adrenergic receptor targeting agent is a selective or non-selective β-blocker.

5. The method of claim 1, wherein the patient has been determined to be homozygous for the nucleic acid encoding asparagine at amino acid 198 of EDN1 protein.

6. The method of claim 1, further comprising genotyping the patient for the nucleic acid encoding the amino acid 198 of EDN1 protein.

* * * * *

SEQUENCE LISTING

<160> NUMBER OF SEQ ID NOS: 21

<210> SEQ ID NO 1
<211> LENGTH: 17
<212> TYPE: DNA
<213> ORGANISM: Homo sapiens

<400> SEQUENCE: 1
caggaaacag ctatgac                                                  17

<210> SEQ ID NO 2
<211> LENGTH: 20
<212> TYPE: DNA
<213> ORGANISM: Homo sapiens

<400> SEQUENCE: 2
cttcttttgc caaagggtga                                               20

<210> SEQ ID NO 3
<211> LENGTH: 20
<212> TYPE: DNA
<213> ORGANISM: Homo sapiens

<400> SEQUENCE: 3
agggtggaga gtgcagagtc                                               20

<210> SEQ ID NO 4
<211> LENGTH: 15
<212> TYPE: DNA
<213> ORGANISM: Homo sapiens

<400> SEQUENCE: 4
ccaagctgaa aggca                                                    15

<210> SEQ ID NO 5
<211> LENGTH: 38
<212> TYPE: DNA
<213> ORGANISM: Homo sapiens

<400> SEQUENCE: 5
caggaaacag ctatgaccag cctttgcctc tctgagtc                           38

<210> SEQ ID NO 6
<211> LENGTH: 21
<212> TYPE: DNA
<213> ORGANISM: Homo sapiens

<400> SEQUENCE: 6
ggccatctga ataactgcaa c                                             21

-continued

```
<210> SEQ ID NO 7
<211> LENGTH: 15
<212> TYPE: DNA
<213> ORGANISM: Homo sapiens

<400> SEQUENCE: 7
gctccccaaa atgat                                                     15

<210> SEQ ID NO 8
<211> LENGTH: 2259
<212> TYPE: DNA
<213> ORGANISM: Homo sapiens

<400> SEQUENCE: 8
aatcagttta acagcctcct gaactccttc ctatcatggt actgccttcc tgttttagag     60
agactaacag agacattgaa agtcagggta aagctgaata taacattgct gaaatgtttt    120
tccttgtgta ttttaacagg gctgaagaca ttatggagaa agactggaat aatcataaga    180
aaggaaaaga ctgttccaag cttgggaaaa agtgtattta tcagcagtta gtgagaggaa    240
gaaaaatcag aagaagttca gaggaacacc taagacaaac caggtaagag ggaaggaaga    300
aaaattaggt aagaggttca caagaacaac tagccccagt cagtgatgcc agcagcctgt    360
tcctccagcc cttcttaccc gggcaggtga aagacttaga aaacagtagc agaggagatc    420
tatgcatcct atagattaaa aggagcaaaa gaatccctct taaatatttc catgaagctc    480
tggaatgcaa accgatgtcc tctgtacttt tagcacatac catttcatct acaggtagat    540
ttcccaacca aaatatatcc agagatgcct tgtcattgg gttatataca gcctttgcct    600
ctctgagtca atgtatttac cactttccct gagaaatcga aaatcatttt ggggagcgga    660
catttagaaa aagaatcaaa gtgtcatgga taatcaaatt cttcaataag ttgcagttat    720
tcagatggcc aaaggaaaaa taaagtcatt agatagggtt ggtagaattt agaacatgct    780 gttttttcagg tttatggtct ttttttttttt tttttttta aatagggaaa tgtgtttggt    840
gcagagccaa tgtcattcca aaaagctctc tcttttcctg gtcagtcatg tgctgggaca    900
gagaagggat ctggattagg caacatcata gagttgctct gagctgctct ttggtgataa    960
cccttccaaa tcctaaactt tttggaattc acaagctcaa aggaggaaac ctactctctg   1020
atctaccaca tgttctgcat ttttctatca tggtctatgg aaacttctct tagaaatcca   1080
gtggcaagaa gttctatgat taaagtgttc tgagctcagg ccaggcagtc atgaactact   1140
tctgagttat ttactactga tttgtggggc agcctcagct atcggtttct tcacacctgc   1200
ttatgagagt atccatattt atggtcgcag gccagtaatg ctccccacga gatcagtttc   1260
tgaactaacc tggaattttt tatgggtttt tattatgcca actattaaat caacattaca   1320
gttcttccct ctgtatttct cctgtaaaac attaggcctg caaaaaaaaa aaatcttttt   1380
aaaaataatt gccataaagt atttgctctg ggcctactgt atgcttcttt tcttttctc    1440 tcttttcaac taagtcaccg tcaatttatt aagatggcca taactattca aaacctatgc   1500
tgagttcctc aaggcagggt cacatagtga tgaaggttgg gatggggcta cggaagaaac   1560
cagaacaact ctagtttatt taaaacctgt atttactgcc cacttcccct tagacttgac   1620
catatgaccc ctcgctccca ttctaagcat aggggcaggc tttatttta caatggtaat   1680 agatatcact tgaggtttta tcaaagagtt gcggcgggtg gtgaaagttc acaaccgat   1740 tcaggttttg tttgtgccag attctaattt tacatgtttc ttttgccaaa gggtgatttt   1800
tttaaaataa catttgtttt ctcttatctt gctttattag gtcggagacc atgagaaaca   1860
```

| | |
|---|---|
| gcgtcaaatc atcttttcat gatcccaagc tgaaaggcaa gccctccaga gagcgttatg | 1920 |
| tgacccacaa ccgagcacat tggtgacaga ccttcgggc ctgtctgaag ccatagcctc | 1980 |
| cacggagagc cctgtggccg actctgcact ctccaccctg gctgggatca gagcaggagc | 2040 |
| atcctctgct ggttcctgac tggcaaagga ccagcgtcct cgttcaaaac attccaagaa | 2100 |
| aggttaagga gttcccccaa ccatcttcac tggcttccat cagtggtaac tgctttggtc | 2160 |
| tcttctttca tctggggatg acaatggacc tctcagcaga aacacacagt cacattcgaa | 2220 |
| ttcgggtggc atcctccgga gagagagaga ggaaggaga | 2259 |

<210> SEQ ID NO 9
<211> LENGTH: 2259
<212> TYPE: DNA
<213> ORGANISM: Homo sapiens

<400> SEQUENCE: 9

| | |
|---|---|
| aatcagttta acagcctcct gaactccttc ctatcatggt actgccttcc tgttttagag | 60 |
| agactaacag agacattgaa agtcaggta aagctgaata taacattgct gaaatgtttt | 120 |
| tccttgtgta ttttaacagg gctgaagaca ttatggagaa agactggaat aatcataaga | 180 |
| aaggaaaaga ctgttccaag cttgggaaaa agtgtattta tcagcagtta gtgagaggaa | 240 |
| gaaaaatcag aagaagttca gaggaacacc taagacaaac caggtaagag ggaaggaaga | 300 |
| aaaattaggt aagaggttca caagaacaac tagccccagt cagtgatgcc agcagcctgt | 360 |
| tcctccagcc cttcttaccc gggcaggtga agacttaga aaacagtagc agaggagatc | 420 |
| tatgcatcct atagattaaa aggagcaaaa gaatccctct taaatatttc catgaagctc | 480 |
| tggaatgcaa accgatgtcc tctgtacttt tagcacatac catttcatct acaggtagat | 540 |
| ttcccaacca aaatatatcc agagatgcct tgtcattgg gttatataca gcctttgcct | 600 |
| ctctgagtca atgtatttac cactttccct gagaaatcga aaatcatttt ggggagcgga | 660 |
| catttagaaa aagaatcaaa gtgtcatgga taatcaaatt cttcaataag ttgcagttat | 720 |
| tcagatggcc aaaggaaaaa taaagtcatt agatagggtt ggtagaattt agaacatgct | 780 |
| gttttttcagg tttatggtct tttttttttt tttttttta aatagggaaa tgtgtttggt | 840 |
| gcagagccaa tgtcattcca aaaagctctc tcttttcctg gtcagtcatg tgctgggaca | 900 |
| gagaagggat ctggattagg caacatcata gagttgctct gagctgctct ttggtgataa | 960 |
| cccttccaaa tcctaaactt tttggaattc acaagctcaa aggaggaaac ctactctctg | 1020 |
| atctaccaca tgttctgcat ttttctatca tggtctatgg aaacttctct tagaaatcca | 1080 |
| gtggcaagaa gttctatgat taaagtgttc tgagctcagg ccaggcagtc atgaactact | 1140 |
| tctgagttat ttactactga tttgtggggc agcctcagct atcggtttct tcacacctgc | 1200 |
| ttatgagagt atccatattt atggtcgcag gccagtaatg ctccccacga gatcagtttc | 1260 |
| tgaactaacc tggaattttt tatgggtttt tattatgcca actattaaat caacattaca | 1320 |
| gttcttccct ctgtatttct cctgtaaaac attaggcctg caaaaaaaaa aaatcttttt | 1380 |
| aaaaataatt gccataaagt atttgctctg ggcctactgt atgcttcttt tcttttctc | 1440 |
| tcttttcaac taagtcaccg tcaatttatt aagatgccca taactattca aaacctatgc | 1500 |
| tgagttcctc aaggcagggt cacatagtga tgaaggttgg gatggggcta cggaagaaac | 1560 |
| cagaacaact ctagtttatt taaaacctgt atttactgcc cacttcccct tagacttgac | 1620 |
| catatgaccc ctcgctccca ttctaagcat aggggcaggc tttatttta caatggtaat | 1680 |
| agatatcact tgaggtttta tcaaagagtt gcggcgggtg gtgaaagttc acaaccagat | 1740 |

| | |
|---|---|
| tcaggttttg tttgtgccag attctaattt tacatgtttc ttttgccaaa gggtgatttt | 1800 |
| tttaaaataa catttgtttt ctcttatctt gctttattag gtcggagacc atgagaaaca | 1860 |
| gcgtcaaatc atcttttcat gatcccaagc tgaaaggcaa ccctccaga gagcgttatg | 1920 |
| tgacccacaa ccgagcacat tggtgacaga ccttcggggc ctgtctgaag ccatagcctc | 1980 |
| cacggagagc cctgtggccg actctgcact ctccaccctg gctgggatca gagcaggagc | 2040 |
| atcctctgct ggttcctgac tggcaaagga ccagcgtcct cgttcaaaac attccaagaa | 2100 |
| aggttaagga gttcccccaa ccatcttcac tggcttccat cagtggtaac tgctttggtc | 2160 |
| tcttctttca tctggggatg acaatggacc tctcagcaga acacacagt cacattcgaa | 2220 |
| ttcgggtggc atcctccgga gagagagaga ggaaggaga | 2259 |

<210> SEQ ID NO 10
<211> LENGTH: 2259
<212> TYPE: DNA
<213> ORGANISM: Homo sapiens

<400> SEQUENCE: 10

| | |
|---|---|
| aatcagttta acagcctcct gaactccttc ctatcatggt actgccttcc tgttttagag | 60 |
| agactaacag agacattgaa agtcagggta aagctgaata taacattgct gaaatgtttt | 120 |
| tccttgtgta ttttaacagg gctgaagaca ttatggagaa agactggaat aatcataaga | 180 |
| aaggaaaaga ctgttccaag cttgggaaaa agtgtattta tcagcagtta gtgagaggaa | 240 |
| gaaaaatcag aagaagttca gaggaacacc taagacaaac caggtaagag ggaaggaaga | 300 |
| aaaattaggt aagaggttca caagaacaac tagccccagt cagtgatgcc agcagcctgt | 360 |
| tcctccagcc cttcttaccc gggcaggtga aagacttaga aaacagtagc agaggagatc | 420 |
| tatgcatcct atagattaaa aggagcaaaa gaatccctct taaatatttc catgaagctc | 480 |
| tggaatgcaa accgatgtcc tctgtacttt tagcacatac catttcatct acaggtagat | 540 |
| ttcccaacca aaatatatcc agagatgcct ttgtcattgg gttatataca gcctttgcct | 600 |
| ctctgagtca atgtatttac cactttccct gagaaatcaa aaatcatttt ggggagcgga | 660 |
| catttagaaa aagaatcaaa gtgtcatgga taatcaaatt cttcaataag ttgcagttat | 720 |
| tcagatggcc aaaggaaaaa taaagtcatt agatagggtt ggtagaattt agaacatgct | 780 |
| gttttttcagg tttatggtct tttttttttt tttttttta aatagggaaa tgtgtttggt | 840 |
| gcagagccaa tgtcattcca aaaagctctc tcttttcctg gtcagtcatg tgctgggaca | 900 |
| gagaagggat ctggattagg caacatcata gagttgctct gagctgctct ttggtgataa | 960 |
| cccttccaaa tcctaaactt tttggaattc acaagctcaa aggaggaaac ctactctctg | 1020 |
| atctaccaca tgttctgcat ttttctatca tggtctatgg aaacttctct tagaaatcca | 1080 |
| gtggcaagaa gttctatgat taaagtgttc tgagctcagg ccaggcagtc atgaactact | 1140 |
| tctgagttat ttactactga tttgtggggc agcctcagct atcggtttct tcacacctgc | 1200 |
| ttatgagagt atccatattt atggtcgcag gccagtaatg ctccccacga gatcagtttc | 1260 |
| tgaactaacc tggaattttt tatgggtttt tattatgcca actattaaat caacattaca | 1320 |
| gttcttccct ctgtatttct cctgtaaaac attaggcctg caaaaaaaaa aaatcttttt | 1380 |
| aaaaataatt gccataaagt atttgctctg ggcctactgt atgcttcttt tcttttctc | 1440 |
| tcttttcaac taagtcaccg tcaatttatt aagatggcca taactattca aaacctatgc | 1500 |
| tgagttcctc aaggcagggt cacatagtga tgaaggttgg gatggggcta cggaagaaac | 1560 |
| cagaacaact ctagttttatt taaaaacctgt atttactgcc cacttcccct tagacttgac | 1620 |

-continued

| | | | | |
|---|---|---|---|---|
| catatgaccc | ctcgctccca | ttctaagcat | aggggcaggc | tttattttta caatggtaat | 1680 |
| agatatcact | tgaggtttta | tcaaagagtt | gcggcgggtg | gtgaaagttc acaaccagat | 1740 |
| tcaggttttg | tttgtgccag | attctaattt | tacatgtttc | ttttgccaaa gggtgatttt | 1800 |
| tttaaaataa | catttgtttt | ctcttatctt | gctttattag | gtcggagacc atgagaaaca | 1860 |
| gcgtcaaatc | atcttttcat | gatcccaagc | tgaaaggcaa | gccctccaga gagcgttatg | 1920 |
| tgacccacaa | ccgagcacat | tggtgacaga | ccttcgggc | ctgtctgaag ccatagcctc | 1980 |
| cacggagagc | cctgtggccg | actctgcact | ctccaccctg | gctgggatca gagcaggagc | 2040 |
| atcctctgct | ggttcctgac | tggcaaagga | ccagcgtcct | cgttcaaaac attccaagaa | 2100 |
| aggttaagga | gttcccccaa | ccatcttcac | tggcttccat | cagtggtaac tgctttggtc | 2160 |
| tcttctttca | tctggggatg | acaatggacc | tctcagcaga | aacacacagt cacattcgaa | 2220 |
| ttcgggtggc | atcctccgga | gagagagaga | ggaaggaga | | 2259 |

<210> SEQ ID NO 11
<211> LENGTH: 2259
<212> TYPE: DNA
<213> ORGANISM: Homo sapiens

<400> SEQUENCE: 11

| | | | | |
|---|---|---|---|---|
| aatcagttta | acagcctcct | gaactccttc | ctatcatggt | actgccttcc tgttttagag | 60 |
| agactaacag | agacattgaa | agtcagggta | aagctgaata | taacattgct gaaatgtttt | 120 |
| tccttgtgta | ttttaacagg | gctgaagaca | ttatggagaa | agactggaat aatcataaga | 180 |
| aaggaaaaga | ctgttccaag | cttgggaaaa | agtgtattta | tcagcagtta gtgagaggaa | 240 |
| gaaaaatcag | aagaagttca | gaggaacacc | taagacaaac | caggtaagag ggaaggaaga | 300 |
| aaaattaggt | aagaggttca | caagaacaac | tagccccagt | cagtgatgcc agcagcctgt | 360 |
| tcctccagcc | cttcttaccc | gggcaggtga | agacttaga | aaacagtagc agaggagatc | 420 |
| tatgcatcct | atagattaaa | aggagcaaaa | gaatccctct | taaatatttc catgaagctc | 480 |
| tggaatgcaa | accgatgtcc | tctgtacttt | tagcacatac | catttcatct acaggtagat | 540 |
| ttcccaacca | aaatatatcc | agagatgcct | tgtcattgg | gttatataca gcctttgcct | 600 |
| ctctgagtca | atgtatttac | cactttccct | gagaaatcaa | aaatcatttt ggggagcgga | 660 |
| catttagaaa | aagaatcaaa | gtgtcatgga | taatcaaatt | cttcaataag ttgcagttat | 720 |
| tcagatggcc | aaaggaaaaa | taaagtcatt | agatagggtt | ggtagaattt agaacatgct | 780 |
| gttttttcagg | tttatggtct | ttttttttttt | ttttttttta | aatagggaaa tgtgtttggt | 840 |
| gcagagccaa | tgtcattcca | aaaagctctc | tcttttcctg | gtcagtcatg tgctgggaca | 900 |
| gagaagggat | ctggattagg | caacatcata | gagttgctct | gagctgctct ttggtgataa | 960 |
| cccttccaaa | tcctaaactt | tttggaattc | acaagctcaa | aggaggaaac ctactctctg | 1020 |
| atctaccaca | tgttctgcat | ttttctatca | tggtctatgg | aaacttctct tagaaatcca | 1080 |
| gtggcaagaa | gttctatgat | taaagtgttc | tgagctcagg | ccaggcagtc atgaactact | 1140 |
| tctgagttat | ttactactga | tttgtggggc | agcctcagct | atcggtttct tcacacctgc | 1200 |
| ttatgagagt | atccatattt | atggtcgcag | gccagtaatg | ctccccacga gatcagtttc | 1260 |
| tgaactaacc | tggaattttt | tatgggtttt | tattatgcca | actattaaat caacattaca | 1320 |
| gttcttccct | ctgtatttct | cctgtaaaac | attaggcctg | caaaaaaaa aaatcttttt | 1380 |
| aaaaataatt | gccataaagt | atttgctctg | ggctactgt | atgcttcttt tctttttctc | 1440 |
| tcttttcaac | taagtcaccg | tcaatttatt | aagatggcca | taactattca aaacctatgc | 1500 |

```
tgagttcctc aaggcagggt cacatagtga tgaaggttgg gatggggcta cggaagaaac    1560
cagaacaact ctagtttatt taaaacctgt atttactgcc cacttcccct tagacttgac    1620
catatgaccc ctcgctccca ttctaagcat aggggcaggc tttattttta caatggtaat    1680
agatatcact tgaggtttta tcaaagagtt gcggcgggtg gtgaaagttc acaaccagat    1740
tcaggttttg tttgtgccag attctaattt tacatgtttc ttttgccaaa gggtgatttt    1800
tttaaaataa catttgtttt ctcttatctt gctttattag gtcggagacc atgagaaaca    1860
gcgtcaaatc atcttttcat gatcccaagc tgaaaggcaa cccctccaga gagcgttatg    1920
tgacccacaa ccgagcacat tggtgacaga ccttcggggc ctgtctgaag ccatagcctc    1980
cacggagagc cctgtggccg actctgcact ctccaccctg gctgggatca gagcaggagc    2040
atcctctgct ggttcctgac tggcaaagga ccagcgtcct cgttcaaaac attccaagaa    2100
aggttaagga gttcccccaa ccatcttcac tggcttccat cagtggtaac tgctttggtc    2160
tcttctttca tctggggatg acaatggacc tctcagcaga aacacacagt cacattcgaa    2220
ttcgggtggc atcctccgga gagagagaga ggaaggaga                           2259

<210> SEQ ID NO 12
<211> LENGTH: 139
<212> TYPE: DNA
<213> ORGANISM: Homo sapiens

<400> SEQUENCE: 12
aatcagttta acagcctcct gaactccttc ctatcatggt actgccttcc tgttttagag      60
agactaacag agacattgaa agtcagggta aagctgaata taacattgct gaaatgtttt     120
tccttgtgta ttttaacag                                                  139

<210> SEQ ID NO 13
<211> LENGTH: 144
<212> TYPE: DNA
<213> ORGANISM: Homo sapiens

<400> SEQUENCE: 13
ggctgaagac attatggaga aagactggaa taatcataag aaaggaaaag actgttccaa      60
gcttgggaaa aagtgtattt atcagcagtt agtgagagga agaaaaatca gaagaagttc     120
agaggaacac ctaagacaaa ccag                                            144

<210> SEQ ID NO 14
<211> LENGTH: 1557
<212> TYPE: DNA
<213> ORGANISM: Homo sapiens

<400> SEQUENCE: 14
gtaagaggga aggaagaaaa attaggtaag aggttcacaa gaacaactag ccccagtcag      60
tgatgccagc agcctgttcc tccagcccct cttacccggg caggtgaaag acttagaaaa     120
cagtagcaga ggagatctat gcatcctata gattaaaagg agcaaaagaa tccctcttaa     180
atatttccat gaagctctgg aatgcaaacc gatgtcctct gtacttttag cacataccat     240
ttcatctaca ggtagatttc ccaaccaaaa tatatccaga gatgcctttg tcattgggtt     300
atatacagcc tttgcctctc tgagtcaatg tatttaccac tttccctgag aaatcgaaaa     360
tcattttggg gagcggacat ttagaaaaag aatcaaagtg tcatggataa tcaaattctt     420
caataagttg cagttattca gatggccaaa ggaaaaataa agtcattaga tagggttggt     480
agaatttaga acatgctgtt tttcaggttt atggtctttt ttttttttttt tttttaaat     540
```

```
agggaaatgt gtttggtgca gagccaatgt cattccaaaa agctctctct tttcctggtc     600
agtcatgtgc tgggacagag aagggatctg gattaggcaa catcatagag ttgctctgag     660
ctgctctttg gtgataaccc ttccaaatcc taaactttt ggaattcaca agctcaaagg     720
aggaaaccta ctctctgatc taccacatgt tctgcatttt tctatcatgg tctatggaaa     780
cttctcttag aaatccagtg gcaagaagtt ctatgattaa agtgttctga gctcaggcca     840
ggcagtcatg aactacttct gagttatta ctactgattt tgggcagc ctcagctatc     900 ggtttcttca cacctgctta tgagagtatc catatttatg gtcgcaggcc agtaatgctc     960
cccacgagat cagtttctga actaacctgg aatttttat gggtttttat tatgccaact    1020
attaaatcaa cattacagtt cttccctctg tatttctcct gtaaaacatt aggcctgcaa    1080
aaaaaaaaaa tctttttaaa aataattgcc ataaagtatt tgctctgggc ctactgtatg    1140
cttcttttct ttttctctct tttcaactaa gtcaccgtca atttattaag atggccataa    1200
ctattcaaaa cctatgctga gttcctcaag gcagggtcac atagtgatga aggttgggat    1260
ggggctacgg aagaaaccag aacaactcta gtttatttaa aacctgtatt tactgcccac    1320
ttccccttag acttgaccat atgacccctc gctcccattc taagcatagg ggcaggcttt    1380 attttttacaa tggtaataga tatcacttga ggttttatca aagagttgcg gcgggtggtg    1440
aaagttcaca accagattca ggttttgttt gtgccagatt ctaattttac atgtttcttt    1500
tgccaaaggg tgatttttt aaaataacat ttgttttctc ttatcttgct ttattag      1557

<210> SEQ ID NO 15
<211> LENGTH: 1557
<212> TYPE: DNA
<213> ORGANISM: Homo sapiens

<400> SEQUENCE: 15
gtaagaggga aggaagaaaa attaggtaag aggttcacaa gaacaactag ccccagtcag     60
tgatgccagc agcctgttcc tccagcccctt cttacccggg caggtgaaag acttagaaaa    120
cagtagcaga ggagatctat gcatcctata gattaaaagg agcaaaagaa tccctcttaa    180
atatttccat gaagctctgg aatgcaaacc gatgtcctct gtacttttag cacataccat    240
ttcatctaca ggtagatttc ccaaccaaaa tatatccaga gatgcctttg tcattgggtt    300
atatacagcc tttgcctctc tgagtcaatg tatttaccac tttccctgag aaatcaaaaa    360
tcattttggg gagcggacat ttagaaaaag aatcaaagtg tcatggataa tcaaattctt    420
caataagttg cagttattca gatggccaaa ggaaaaataa agtcattaga tagggttggt    480
agaatttaga acatgctgtt tttcaggttt atggtctttt tttttttttt tttttaaat    540 agggaaatgt gtttggtgca gagccaatgt cattccaaaa agctctctct tttcctggtc     600
agtcatgtgc tgggacagag aagggatctg gattaggcaa catcatagag ttgctctgag     660
ctgctctttg gtgataaccc ttccaaatcc taaactttt ggaattcaca agctcaaagg     720
aggaaaccta ctctctgatc taccacatgt tctgcatttt tctatcatgg tctatggaaa     780
cttctcttag aaatccagtg gcaagaagtt ctatgattaa agtgttctga gctcaggcca     840
ggcagtcatg aactacttct gagttatta ctactgattt tgggcagc ctcagctatc     900 ggtttcttca cacctgctta tgagagtatc catatttatg gtcgcaggcc agtaatgctc     960
cccacgagat cagtttctga actaacctgg aatttttat gggtttttat tatgccaact    1020
attaaatcaa cattacagtt cttccctctg tatttctcct gtaaaacatt aggcctgcaa    1080
aaaaaaaaaa tctttttaaa aataattgcc ataaagtatt tgctctgggc ctactgtatg    1140
```

```
cttcttttct ttttctctct tttcaactaa gtcaccgtca atttattaag atggccataa    1200
ctattcaaaa cctatgctga gttcctcaag gcagggtcac atagtgatga aggttgggat    1260
ggggctacgg aagaaaccag acaactcta gtttatttaa aacctgtatt tactgcccac    1320
ttccccttag acttgaccat atgacccctc gctcccattc taagcatagg ggcaggcttt    1380 attttttacaa tggtaataga tatcacttga ggttttatca aagagttgcg gcgggtggtg    1440
aaagttcaca accagattca ggttttgttt gtgccagatt ctaattttac atgtttcttt    1500
tgccaaaggg tgatttttt aaaataacat ttgttttctc ttatcttgct ttattag       1557

<210> SEQ ID NO 16
<211> LENGTH: 419
<212> TYPE: DNA
<213> ORGANISM: Homo sapiens

<400> SEQUENCE: 16
gtcggagacc atgagaaaca gcgtcaaatc atcttttcat gatcccaagc tgaaaggcaa      60
gccctccaga gagcgttatg tgacccacaa ccgagcacat tggtgacaga ccttcggggc     120
ctgtctgaag ccatagcctc cacggagagc cctgtggccg actctgcact ctccaccctg     180
gctgggatca gagcaggagc atcctctgct ggttcctgac tggcaaagga ccagcgtcct     240
cgttcaaaac attccaagaa aggttaagga gttcccccaa ccatcttcac tggcttccat     300
cagtggtaac tgctttggtc tcttctttca tctggggatg acaatggacc tctcagcaga     360
aacacacagt cacattcgaa ttcgggtggc atcctccgga gagagagaga ggaaggaga      419

<210> SEQ ID NO 17
<211> LENGTH: 419
<212> TYPE: DNA
<213> ORGANISM: Homo sapiens

<400> SEQUENCE: 17
gtcggagacc atgagaaaca gcgtcaaatc atcttttcat gatcccaagc tgaaaggcaa      60
cccctccaga gagcgttatg tgacccacaa ccgagcacat tggtgacaga ccttcggggc     120
ctgtctgaag ccatagcctc cacggagagc cctgtggccg actctgcact ctccaccctg     180
gctgggatca gagcaggagc atcctctgct ggttcctgac tggcaaagga ccagcgtcct     240
cgttcaaaac attccaagaa aggttaagga gttcccccaa ccatcttcac tggcttccat     300
cagtggtaac tgctttggtc tcttctttca tctggggatg acaatggacc tctcagcaga     360
aacacacagt cacattcgaa ttcgggtggc atcctccgga gagagagaga ggaaggaga      419

<210> SEQ ID NO 18
<211> LENGTH: 21
<212> TYPE: DNA
<213> ORGANISM: Homo sapiens

<400> SEQUENCE: 18
cagcctttgc ctctctgagt c                                               21

<210> SEQ ID NO 19
<211> LENGTH: 21
<212> TYPE: DNA
<213> ORGANISM: Homo sapiens

<400> SEQUENCE: 19
gttgcagtta ttcagatggc c                                               21
```

```
<210> SEQ ID NO 20
<211> LENGTH: 19
<212> TYPE: DNA
<213> ORGANISM: Homo sapiens

<400> SEQUENCE: 20
ttcttttgcc aaagggtga                                            19

<210> SEQ ID NO 21
<211> LENGTH: 20
<212> TYPE: DNA
<213> ORGANISM: Homo sapiens

<400> SEQUENCE: 21
gactctgcac tctccaccct                                           20
```